(12) United States Patent
Harari et al.

(10) Patent No.: US 9,675,780 B2
(45) Date of Patent: Jun. 13, 2017

(54) BALLOON CATHETER SYSTEM AND METHODS OF MAKING AND USE THEREOF

(75) Inventors: Eran Harari, Maagan Michael (IL); Alexander Barash, Tzoran (IL); Gil Bernstein, Kiryat Ono (IL)

(73) Assignee: AngioSlide Ltd., Natania (IL)

( * ) Notice: Subject to any disclaimer, the term of this patent is extended or adjusted under 35 U.S.C. 154(b) by 659 days.

(21) Appl. No.: 13/522,717

(22) PCT Filed: Jan. 19, 2011

(86) PCT No.: PCT/IL2011/000060
§ 371 (c)(1),
(2), (4) Date: Sep. 19, 2012

(87) PCT Pub. No.: WO2011/089599
PCT Pub. Date: Jul. 28, 2011

(65) Prior Publication Data
US 2013/0006291 A1 Jan. 3, 2013

Related U.S. Application Data

(60) Provisional application No. 61/296,113, filed on Jan. 19, 2010.

(51) Int. Cl.
*A61M 29/00* (2006.01)
*A61M 25/00* (2006.01)
(Continued)

(52) U.S. Cl.
CPC .... *A61M 25/0097* (2013.01); *A61M 25/1006* (2013.01); *A61M 25/1018* (2013.01);
(Continued)

(58) Field of Classification Search
CPC ............... A61M 25/10; A61M 25/104; A61M 25/1018; A61M 25/10181;
(Continued)

(56) References Cited

U.S. PATENT DOCUMENTS

| 4,004,588 A | 1/1977 | Alexander |
| 4,243,040 A | 1/1981 | Beecher |

(Continued)

FOREIGN PATENT DOCUMENTS

| CA | 2183214 | 2/1998 |
| CN | 1322145 | 11/2001 |

(Continued)

OTHER PUBLICATIONS

Supplementary European Search Report Dated Jul. 1, 2016 From the European Patent Office Re. Application No. 13861353.4.

(Continued)

*Primary Examiner* — Tuan V Nguyen

(57) ABSTRACT

A catheter system having an intussuscepting balloon and a handle for a catheter system. The handle includes a fluidic system for preventing overpressure conditions during balloon intussuscepting and includes a locking mechanism disposed outside of the fluidic system for preventing unintended or accidental movements of a plunger assembly included in the fluidic system. The system includes standard sized components and non-standard sized components. During handle assembly, specific sizes of non-standard sized components are selected to match the length and/or the diameter of a specific selected balloon and are assembled with the standard sized components to form the catheter system.

41 Claims, 12 Drawing Sheets

(51) Int. Cl.
*A61M 25/10* (2013.01)
*A61M 25/01* (2006.01)

(52) U.S. Cl.
CPC .. *A61M 25/1027* (2013.01); *A61M 25/10181* (2013.11); *A61M 25/10184* (2013.11); *A61M 2025/0004* (2013.01); *A61M 2025/0175* (2013.01); *A61M 2025/1065* (2013.01); *Y10T 29/49826* (2015.01)

(58) Field of Classification Search
CPC ...... A61M 25/10184; A61M 25/10185; A61M 25/1006; A61M 25/0119; A61M 25/0097
USPC ...................................................... 623/1.11
See application file for complete search history.

(56) References Cited

U.S. PATENT DOCUMENTS

| | | | |
|---|---|---|---|
| 4,271,839 A | 6/1981 | Fogarty et al. | |
| 4,469,100 A | 9/1984 | Hardwick et al. | |
| 4,597,389 A | 7/1986 | Ibrahim | |
| 4,611,594 A | 9/1986 | Grayhack et al. | |
| 4,748,982 A | 6/1988 | Horzewski et al. | |
| 4,762,129 A | 8/1988 | Bonzel | |
| 4,820,270 A | 4/1989 | Hardcastle et al. | |
| 4,846,174 A * | 7/1989 | Willard et al. | 606/194 |
| 4,946,440 A | 8/1990 | Hall | |
| 4,955,895 A | 9/1990 | Sugiyama et al. | |
| 4,968,300 A * | 11/1990 | Moutafis et al. | 604/103.07 |
| 5,019,041 A | 5/1991 | Robinson et al. | |
| 5,074,845 A | 12/1991 | Miraki et al. | |
| 5,092,839 A | 3/1992 | Kipperman | |
| 5,109,830 A | 5/1992 | Cho | |
| 5,254,091 A | 10/1993 | Aliahmad et al. | |
| 5,307,814 A | 5/1994 | Kressel et al. | |
| RE34,633 E | 6/1994 | Sos et al. | |
| 5,338,298 A | 8/1994 | McIntyre | |
| 5,421,826 A | 6/1995 | Crocker et al. | |
| 5,437,638 A | 8/1995 | Bowman | |
| 5,445,646 A | 8/1995 | Euteneuer et al. | |
| 5,470,314 A | 11/1995 | Walinsky | |
| 5,534,007 A | 7/1996 | St. Germain et al. | |
| 5,630,822 A | 5/1997 | Hermann et al. | |
| 5,785,675 A | 7/1998 | Drasler et al. | |
| 5,865,801 A | 2/1999 | Houser | |
| 5,868,767 A | 2/1999 | Farley et al. | |
| 5,941,895 A | 8/1999 | Myler et al. | |
| 5,968,012 A | 10/1999 | Ren et al. | |
| 6,004,341 A | 12/1999 | Zhu et al. | |
| 6,022,359 A | 2/2000 | Frantzen | |
| 6,039,721 A | 3/2000 | Johnson et al. | |
| 6,063,057 A * | 5/2000 | Choh | 604/99.01 |
| 6,129,706 A | 10/2000 | Janacek | |
| 6,152,947 A | 11/2000 | Ambrisco et al. | |
| 6,159,230 A | 12/2000 | Samuels | |
| 6,179,827 B1 | 1/2001 | Davis et al. | |
| 6,280,412 B1 | 8/2001 | Pederson, Jr. et al. | |
| 6,383,195 B1 | 5/2002 | Richard | |
| 6,695,810 B2 | 2/2004 | Peacock, III et al. | |
| 7,172,576 B2 | 2/2007 | Sawa et al. | |
| 7,201,770 B2 | 4/2007 | Johnson et al. | |
| 7,563,270 B2 | 7/2009 | Gumm | |
| 7,591,831 B2 | 9/2009 | Parsonage et al. | |
| 7,824,345 B2 | 11/2010 | Euteneuer et al. | |
| 7,824,370 B2 | 11/2010 | Hirszowicz et al. | |
| 8,556,851 B2 | 10/2013 | Hirszowicz et al. | |
| 2002/0082639 A1 | 6/2002 | Broome et al. | |
| 2002/0091398 A1 | 7/2002 | Galdonik et al. | |
| 2002/0121472 A1 | 9/2002 | Garner et al. | |
| 2002/0177870 A1 | 11/2002 | Sepetka et al. | |
| 2003/0028211 A1 | 2/2003 | Crocker et al. | |
| 2003/0055483 A1 | 3/2003 | Gumm | |
| 2003/0093107 A1 | 5/2003 | Parsonage et al. | |
| 2003/0105508 A1 | 6/2003 | Johnson et al. | |
| 2003/0130672 A1 | 7/2003 | Dobrava et al. | |
| 2003/0176884 A1 | 9/2003 | Berrada et al. | |
| 2003/0176910 A1 | 9/2003 | Vrba et al. | |
| 2003/0208223 A1 | 11/2003 | Kleiner | |
| 2004/0049223 A1 | 3/2004 | Nishtala et al. | |
| 2004/0054362 A1 | 3/2004 | Lopath et al. | |
| 2004/0073243 A1 | 4/2004 | Sepetka et al. | |
| 2004/0236275 A1 | 11/2004 | Pruitt et al. | |
| 2004/0236367 A1 | 11/2004 | Brown et al. | |
| 2005/0004553 A1 | 1/2005 | Douk | |
| 2005/0085826 A1 | 4/2005 | Nair et al. | |
| 2005/0101986 A1 | 5/2005 | Daniel et al. | |
| 2005/0102019 A1 | 5/2005 | Yadin | |
| 2005/0137501 A1 | 6/2005 | Euteneuer et al. | |
| 2005/0137607 A1 | 6/2005 | Assell et al. | |
| 2005/0154414 A1 | 7/2005 | Perreault et al. | |
| 2005/0187570 A1 | 8/2005 | Nguyen et al. | |
| 2005/0209629 A1 | 9/2005 | Kerr et al. | |
| 2005/0261705 A1 | 11/2005 | Gist | |
| 2005/0288700 A1 | 12/2005 | Chermoni | |
| 2006/0015134 A1 | 1/2006 | Trinidad | |
| 2006/0025720 A1 | 2/2006 | Sawa et al. | |
| 2006/0129107 A1 | 6/2006 | McArthur et al. | |
| 2006/0129710 A1 | 6/2006 | O'Connor et al. | |
| 2007/0083158 A1 * | 4/2007 | Hirszowicz et al. | 604/96.01 |
| 2007/0088380 A1 | 4/2007 | Hirszowicz et al. | |
| 2007/0255305 A1 | 11/2007 | McMichael et al. | |
| 2008/0051706 A1 | 2/2008 | Hirszowicz et al. | |
| 2009/0112239 A1 | 4/2009 | To | |
| 2009/0171278 A1 | 7/2009 | Hirszowicz et al. | |
| 2009/0204069 A1 | 8/2009 | Hirszowicz et al. | |
| 2009/0247945 A1 | 10/2009 | Levit et al. | |
| 2009/0270902 A1 | 10/2009 | Assell et al. | |
| 2010/0010303 A1 | 1/2010 | Bakos | |
| 2010/0016792 A1 | 1/2010 | Hirszowicz | |
| 2010/0022970 A1 | 1/2010 | Hirszowicz | |
| 2011/0040365 A1 | 2/2011 | Hirszowicz et al. | |
| 2011/0275990 A1 | 11/2011 | Besser et al. | |
| 2012/0302996 A1 | 11/2012 | Barash et al. | |
| 2013/0060234 A1 | 3/2013 | Besser et al. | |
| 2015/0126966 A1 | 5/2015 | Hirszowicz et al. | |
| 2015/0306361 A1 | 10/2015 | Feig et al. | |

FOREIGN PATENT DOCUMENTS

| | | |
|---|---|---|
| CN | 101583318 | 11/2009 |
| CN | 101972510 | 2/2011 |
| CN | 102131471 | 7/2011 |
| EP | 0200668 | 12/1986 |
| EP | 359 489 | 3/1990 |
| EP | 0366478 | 5/1990 |
| EP | 380873 | 8/1990 |
| EP | 0399712 | 11/1990 |
| EP | 0987045 | 3/2000 |
| EP | 1120129 | 8/2001 |
| EP | 1124504 | 8/2001 |
| EP | 1333778 | 8/2003 |
| EP | 1062966 | 9/2004 |
| EP | 1753348 | 2/2007 |
| GB | 2054385 | 2/1981 |
| IL | 178738 | 2/2007 |
| JP | 54-066582 A | 5/1979 |
| JP | 59-502134 | 12/1984 |
| JP | 61-293474 | 12/1986 |
| JP | 02-119875 | 5/1990 |
| JP | 2000005189 A | 1/2000 |
| JP | 2002-520099 | 7/2002 |
| JP | 2003-126263 | 5/2003 |
| JP | 2004-329485 | 11/2004 |
| WO | WO 84/01513 | 4/1984 |
| WO | WO 95/17223 | 6/1995 |
| WO | WO 98/29026 | 7/1998 |
| WO | WO 00/02613 | 1/2000 |
| WO | WO 00/27309 | 5/2000 |
| WO | WO 00 38776 | 7/2000 |
| WO | WO 02/38084 | 5/2002 |
| WO | WO 02/055146 | 7/2002 |
| WO | WO 2004/014240 | 2/2004 |
| WO | WO 2004/017865 | 3/2004 |
| WO | WO 2004/028611 | 4/2004 |

(56) References Cited

FOREIGN PATENT DOCUMENTS

| WO | WO 2004/082462 | 9/2004 |
|---|---|---|
| WO | WO 2004/098681 | 11/2004 |
| WO | WO 2005/000130 | 1/2005 |
| WO | WO 2005/030308 | 4/2005 |
| WO | WO 2005/041788 | 5/2005 |
| WO | WO 2005/102184 | 11/2005 |
| WO | WO 2005/112783 | 12/2005 |
| WO | WO 2007/004221 | 1/2007 |
| WO | WO 2007/042935 | 4/2007 |
| WO | WO 2007/042936 | 4/2007 |
| WO | WO 2007/132464 | 11/2007 |
| WO | WO 2008/004238 | 1/2008 |
| WO | WO 2008/004239 | 1/2008 |
| WO | WO 2009/053839 | 4/2009 |
| WO | WO 2010/001404 | 1/2010 |
| WO | WO 2010/001405 | 1/2010 |
| WO | WO 2010/079494 | 7/2010 |
| WO | WO 2011/036667 | 3/2011 |
| WO | WO 2011/080731 | 7/2011 |
| WO | WO 2011/080732 | 7/2011 |
| WO | WO 2011/089599 | 7/2011 |
| WO | WO 2014/087395 | 6/2014 |
| WO | WO 2016/199117 | 12/2016 |

OTHER PUBLICATIONS

Communication Pursuant to Article 94(3) and Rule 71(1) EPC Dated Mar. 16, 2011 From the European Patent Office Re. Application No. 07766874.7.
Communication Pursuant to Article 94(3) EPC Dated Apr. 4, 2012 From the European Patent Office Re. Application No. 10170623.2.
Communication Pursuant to Article 94(3) EPC Dated Mar. 10, 2011 From the European Patent Office Re. Application No. 07766875.4.
Communication Pursuant to Article 94(3) EPC Dated Feb. 23, 2010 From the European Patent Office Re. Application No. 07766875.4.
Communication Pursuant to Article 94(3) EPC Dated Jan. 28, 2010 From the European Patent Office Re. Application No. 07766874.7.
Communication Pursuant to Article 94(3) EPC Dated Dec. 29, 2008 From the European Patent Office Re. Application No. 05735055.5.
Communication Pursuant to Article 94(3) EPC Dated May 29, 2008 From the European Patent Office Re. Application No. 06766111.6.
Communication Pursuant to Article 94(3) EPC Dated Aug. 30, 2011 From the European Patent Office Re. Application No. 10170623.2.
Communication Pursuant to Article 96(2) EPC Dated Nov. 5, 2007 From the European Patent Office Re. Application No. 05735055.5.
Decision of Patent Dated Mar. 6, 2012 From the Japanese Patent Office Re. Application No. 2007-509059 and Its Translation Into English.
Decision to Grant A European Patent Pursuant to Article 97(1) EPC Dated Aug. 12, 2010 From the European Patent Office Re. Application No. 10170623.2.
Decision to Grant A European Patent Pursuant to Article 97(1) EPC Dated Aug. 17, 2012 From the European Patent Office Re. Application No. 10169255.6.
Decision to Grant A European Patent Pursuant to Article 97(1) EPC Dated Jul. 19, 2010 From the European Patent Office Re. Application No. 05735055.5.
European Search Report and the European Search Opinion Dated Nov. 15, 2010 From the European Patent Office Re. Application No. 10169255.6.
European Search Report and the European Search Opinion Dated Nov. 26, 2010 From the European Patent Office Re. Application No. 10170623.2.
Examination Report Dated Dec. 31, 2012 From the Government of India, Patent Office, Intellectual Property Building Re. Application No. 3402/KOLNP/2006.
Examiner's Report Dated Feb. 2, 2011 From the Australian Government, IP Australia Re. Application No. 2006264397.

Final Rejection Dated Aug. 30, 2011 From the Japanese Patent Office Re. Application No. 2007-509059 and Its Translation Into English.
International Preliminary Report on Patentability Dated Jul. 4, 2012 From the International Bureau of WIPO Re. Application No. PCT/IL2010/000002.
International Preliminary Report on Patentability Dated Jan. 5, 2011 From the International Bureau of WIPO Re. Application No. PCT/IL2009/000667.
International Preliminary Report on Patentability Dated Jan. 5, 2011 From the International Bureau of WIPO Re. Application No. PCT/IL2009/000668.
International Preliminary Report on Patentability Dated Apr. 7, 2007 From the International Bureau of WIPO Re. Application No. PCT/iL2007/000845.
International Preliminary Report on Patentability Dated Apr. 7, 2009 From the International Bureau of WIPO Re. Application No. PCT/IL2007/000844.
International Preliminary Report on Patentability Dated Jan. 9, 2008 From the International Bureau of WIPO Re. Application No. PCT/IL2006/000770.
International Preliminary Report on Patentability Dated Jun. 9, 2015 From the International Bureau of WIPO Re. Application No. PCT/IL2013/000089.
International Preliminary Report on Patentability Dated Mar. 10, 2009 From the International Bureau of WIPO Re. Application No. PCT/IB2006/002955.
International Preliminary Report on Patentability Dated Jul. 12, 2011 From the International Bureau of WIPO Re. Application No. PCT/IL2009/000667.
International Preliminary Report on Patentability Dated Jul. 24, 2012 From the International Bureau of WIPO Re. Application No. PCT/1L2011/000060.
International Preliminary Report on Patentability Dated Oct. 25, 2006 From the International Bureau of WIPO Re. Application No. PCT/IL2005/000420.
International Preliminary Report on Patentability Dated Mar. 27, 2012 From the International Bureau of WIPO Re. Application No. PCT/IL2010/000797.
International Search Report and the Written Opinion Dated Jun. 1, 2010 From the International Searching Authority Re. Application No. PCT/IL2010/000025.
International Search Report and the Written Opinion Dated Nov. 3, 2006 From the International Searching Authority Re. Application No. PCT/IL2006/000770.
International Search Report and the Written Opinion Dated May 7, 2010 From the International Searching Authority Re. Application No. PCT/IL2010/000001.
International Search Report and the Written Opinion Dated Aug. 11, 2008 From the International Searching Authority Re. Application No. PCT/IL2007/000844.
International Search Report and the Written Opinion Dated Aug. 11, 2008 From the International Searching Authority Re. Application No. PCT/IL2007/000845.
International Search Report and the Written Opinion Dated May 12, 2010 From the International Searching Authority Re. Application No. PCT/IL2010/000002.
International Search Report and the Written Opinion Dated Feb. 23, 2011 From the International Searching Authority Re. Application No. PCT/iL2010/000797.
international Search Report and the Written Opinion Dated May 23, 2011 From the International Searching Authority Re. Application No. PCT/IL2011/000060.
International Search Report and the Written Opinion Dated Mar. 26, 2014 From the International Searching Authority Re. Application No. PCT/IL2013/000089.
International Search Report and the Written Opinion Dated Oct. 28, 2009 From the International Searching Authority Re. Application No. PCT/IL2009/000667.
International Search Report and the Written Opinion Dated Oct. 28, 2009 From the International Searching Authority Re. Application No. PCT/IL2009/000668.

(56) References Cited

OTHER PUBLICATIONS

International Search Report and the Written Opinion Dated Jul. 29, 2005 From the International Searching Authority Re. Application No. PCT/IL2005/000420.
International Search Report and the Written Opinion Dated Oct. 29, 2008 From the International Searching Authority Re. Application No. PCT/IB2006/002955.
Invitation Pursuant to Article 94(3) and Rule 71(1) EPC Dated Dec. 19, 2013 From the European Patent Office Re. Application No. 10170623.2.
Notice of Allowance Dated Jul. 3, 2013 From the U.S. Appl. No. 13/001,433.
Notice of Allowance Dated May 6, 2014 From the U.S. Appl. No. 13/001,433.
Notice of Allowance Dated Nov. 8, 2012 From the U.S. Appl. No. 12/901,535.
Notice of Allowance Dated Jul. 9, 2012 From the U.S. Appl. No. 12/901,535.
Notice of Allowance Dated Nov. 12, 2013 From the U.S. Appl. No. 13/001,433.
Notice of Allowance Dated Jul. 23, 2014 From the U.S. Appl. No. 12/083,436.
Notice of Refusal Dated May 19, 2014 From the Israel Patent Office Re. Application No. 211022.
Notice of the Reason for Rejection Dated May 13, 2013 From the Korean Intellectual Property Office Re. Application No. 10-2008-7010935.
Notification of Gorunds for Rejection Dated Aug. 16, 2011 From the Japanese Patent Office Re. Application No. 2008-519139 and Its Translation Into English.
Notification of Grounds for Rejection Dated Oct. 25, 2011 From the Japanese Patent Office Re. Application No. 2008-535127 and Its Translation Into English.
Notification of Office Action Dated Oct. 24, 2012 From the State Intellectual Property Office of the People's Republic of China Re. Application No. 200980132738.0.
Notification of the Decision to Grant a Patent Right for Patent for Invention Dated Mar. 6, 2013 From the Patent Office of the People's Republic of China Re. Application No. 201010224944.9 and Its Translation Into English.
Notification of the Decision to Grant a Patent Right for Patent for Invention Dated Apr. 20, 2010 From the Patent Office of the People's Republic of China Re. Application No. 200580020733.0 and Its Translation Into English.
Office Action and Search Report Dated Apr. 2, 2013 From the State Intellectual Property Office of the People's Republic of China Re. Application No. 201210018835.0 and Its Translation Into English.
Office Action and Search Report Dated Aug. 4, 2014 From the State Intellectual Property Office of the People's Republic of China Re. Application No. 201310193577.4 and Its Translation Into English.
Office Action and Search Report Dated Aug. 31, 2012 From the State Intellectual Property Office of the People's Republic of China Re. Application No. 201010224944.9 and Its Translation Into English.
Office Action Dated Sep. 2, 2014 From the State Intellectual Property Office of the People's Republic of China Re. Application No. 201210018835.0 and Its Translation Into English.
Office Action Dated Mar. 5, 2012 From the Israel Patent Office Re. Application No. 178738.
Office Action Dated Mar. 5, 2012 From the Israel Patent Office Re. Application No. 211022.
Office Action Dated Jun. 6, 2012 From the Israel Patent Office Re. Application No. 211023.
Office Action Dated Mar. 6, 2012 From the State Intellectual Property Office of the People's Republic of China Re. Application No. 200680032507.9 and Its Translation Into English.
Office Action Dated Oct. 8, 2012 From the State Intellectual Property Office of the People's Republic of China Re. Application No. 200680047235.X and Its Translation Into English.
Office Action Dated Nov. 9, 2009 From the Israel Patent Office Re. Application No. 178738.
Office Action Dated Aug. 12, 2011 From the State Intellectual Property Office of the People's Republic of China Re. Application No. 200680032507.9 and Its Translation Into English.
Office Action Dated Jan. 12, 2012 From the State Intellectual Property Office of the People's Republic of China Re. Application No. 201010224944.9 and Its Translation Into English.
Office Action Dated Jun. 12, 2009 From the State Intellectual Property Office of the People's Republic of China Re. Application No. 200580020733.0 and Its Translation Into English.
Office Action Dated Apr. 13, 2015 From the State Intellectual Property Office of the People's Republic of China Re. Application No. 201310193577.4 and Its Translation Into English.
Office Action Dated Mar. 17, 2011 From the Israel Patent Office Re. Application No. 178738.
Office Action Dated Jun. 23, 2011 From the State Intellectual Property Office of the People's Republic of China Re. Application No. 201010224944.9 and its Translation Into English.
Office Action Dated Oct. 23, 2009 From the State Intellectual Property Office of the People's Republic of China Re. Application No. 200680032507.9 and Its Translation Into English.
Office Action Dated Dec. 24, 2013 From the State Intellectual Property Office of the People's Republic of China Re. Application No. 201210018835.0 and Its Translation Into English.
Office Action Dated Oct. 25, 2011 From the State Intellectual Property Office of the People's Republic of China Re. Application No. 200680047235.X and Its Translation Into English.
Official Action Dated Dec. 5, 2011 From the U.S. Appl. No. 12/901,535.
Official Action Dated Dec. 8, 2009 From the U.S. Appl. No. 11/587,179.
Official Action Dated Aug. 18, 2010 From the U.S. Appl. No. 12/083,436.
Official Action Dated Jul. 19, 2012 From the U.S. Appl. No. 12/083,436.
Official Action Dated Apr. 20, 2015 From the U.S. Appl. No. 13/497,055.
Official Action Dated May 20, 2011 From the U.S. Appl. No. 12/083,436.
Official Action Dated Dec. 21, 2012 From the U.S. Appl. No. 13/001,433.
Official Action Dated Jan. 25, 2016 From the U.S. Appl. No. 14/012,624.
Official Action Dated Sep. 26, 2014 From the U.S. Appl. No. 13/497,055.
Requisition by the Examiner Dated Feb. 7, 2012 From the Canadian Intellectual Property Office Re. Application No. 2,563,657.
Requisition by the Examiner Dated Mar. 19, 2013 From the Canadian Intellectual Property Office Re. Application No. 2,613,713.
Restriction Official Action Dated May 13, 2009 From the U.S. Appl. No. 11/587,179.
Restriction Official Action Dated Jan. 20, 2011 From the U.S. Appl. No. 12/306,934.
Restriction Official Action Dated Jan. 21, 2011 From the U.S. Appl. No. 12/306,933.
Restriction Official Action Dated Oct. 25, 2012 From the U.S. Appl. No. 13/001,433.
Statement of Opinion Dated Sep. 10, 2013 From the Korean Intellectual Property Office Re. Application No. 10-2008-7001219 and Its Translation Into English.
Supplementary European Search Report and the European Search Opinion Dated Nov. 8, 2013 From the European Patent Office Re. Application No. 06809092.7.
Supplementary European Search Report and the European Search Opinion Dated Sep. 16, 2011 From the European Patent Office Re. Application No. 09773059.2.
Supplementary European Search Report and the European Search Opinion Dated Jul. 18, 2011 From the European Patent Office Re. Application No. 09773060.0.
Supplementary Partial European Search Report and the European Search Opinion Dated Nov. 19, 2009 From the European Patent Office Re. Application No. 07766875.4.

(56) References Cited

OTHER PUBLICATIONS

Supplementary Partial European Search Report and the European Search Opinion Dated Oct. 19, 2009 From the European Patent Office Re. Application No. 07766874.7.
Translation of Notice of Reasons for Rejection Dated Dec. 14, 2010 From the Japanese Patent Office Re. Application No. 2007-509059.
Translation of Office Action Dated Sep. 19, 2010 From the State Intellectual Property Office of the People's Republic of China Re. Application No. 200680032507.9.
Translation of Office Action Dated Jan. 21, 2013 From the State Intellectual Property Office of the People's Republic of China Re. Application No. 200680032507.9.
Translation of Rejection Decision Dated Aug. 31, 2012 From the State Intellectual Property Office of the People's Republic of China Re. Application No. 200680032507.9.
Examination Report Under Sections 12 & 13 of the Patents Act, 1970 and the Patents Rules, 2003 Dated May 10, 2016 From the Government of India, Patent Office, Intellectual Property Building Re. Application No. 439/KOLNP/2008.
Notice of Allowance Dated Jun. 7, 2013 From the U.S. Appl. No. 11/477,812.
Official Action Dated Jul. 6, 2012 From the U.S. Appl. No. 11/477,812.
Official Action Dated Feb. 23, 2011 From the U.S. Appl. No. 11/477,812.
Official Action Dated Nov. 28, 2011 From the U.S. Appl. No. 11/477,812.
Restriction Official Action Dated Sep. 13, 2010 From the U.S. Appl. No. 11/477,812.
Restriction Official Action Dated Sep. 23, 2016 From the U.S. Appl. No. 14/551,866.
Restriction Official Action Dated Aug. 2, 2016 From the U.S. Appl. No. 13/520,345.
International Search Report and the Written Opinion Dated Oct. 13, 2015 From the International Searching Authority Re. Application No. PCT/IL2015/050582.
Notice of Allowance Dated Jun. 25, 2010 From the U.S. Appl. No. 11/587,179.
Communication Pursuant to Article 94(3) EPC Dated Feb. 3, 2017 From the European Patent Office Re. Application No. 13861353.4. (7 pages).
Office Action and Search Report Dated Jan. 4, 2017 From the State Intellectual Property Office of the People's Republic of China Re. Application No. 201380071889.6 and Its Translation Into English. (12 Pages).
Official Action Dated Dec. 19, 2016 From the US Patent and Trademark Office Re. U.S. Appl. No. 14/551,866. (41 pages).

\* cited by examiner

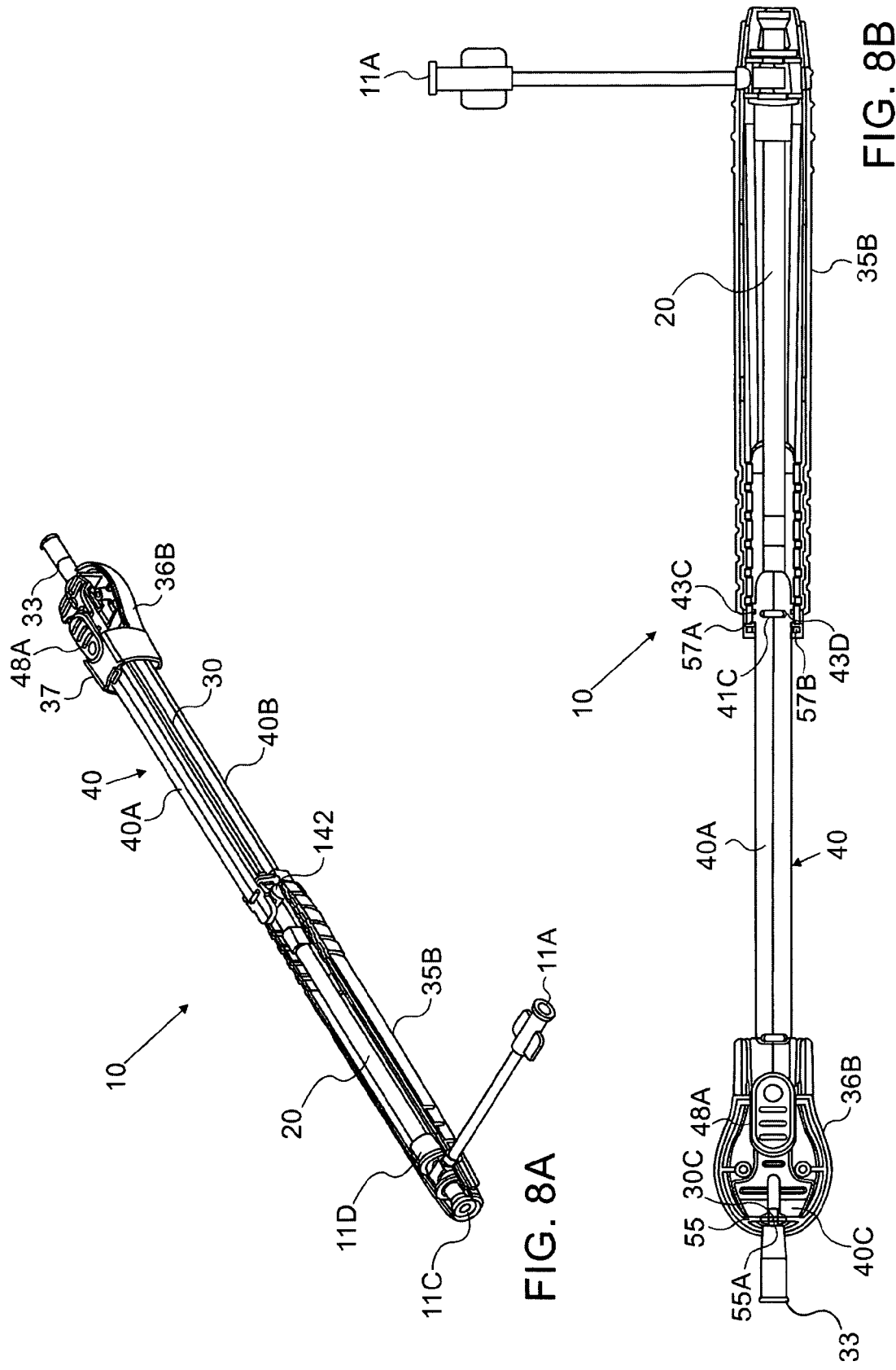

BALLOON CATHETER SYSTEM AND METHODS OF MAKING AND USE THEREOF

CROSS-REFERENCE TO RELATED APPLICATIONS

This application is a U.S. National Phase Application under 35 U.S.C. 371 of PCT International Application No. PCT/IL2011/000060, which has an international filing date of Jan. 19, 2011, and which claims priority benefit of U.S. Provisional Patent Application No. 61/296,113, filed Jan. 19, 2010, the contents of which are incorporated herein by reference in their entirety.

FIELD OF THE INVENTION

The present disclosure generally relates to the field of medical balloon catheters and in particular to balloon catheter systems having intussuscepting inflatable elements, and methods of constructing and use of such catheter balloon systems.

BACKGROUND OF THE INVENTION

Catheters are used in various interventional procedures for delivering therapeutic means to a treated site (e.g., body organ or passageway such as blood vessels). In many cases, a catheter with a small distal inflatable balloon is guided to the treated site. Once the balloon is in place it is inflated by the operator for affixing it in place, for expanding a blocked vessel, for placing treatment means (e.g., stent) and/or for delivering surgical tools (e.g. knives, drills etc.) to a desired site. In addition, catheter systems have also been designed and used for retrieval of objects such as stents from body passageways.

A type of catheter developed for intravascular use is an over-the-wire (OVT) catheter. OVT catheter systems are characterized by the presence of a full-length guide wire, such that when the catheter is in its in situ working position, said guide wire passes through the entire length of a lumen formed in, or externally attached to, the catheter. OVT systems have several operational advantages which are related to the use of a full length guide wire, including good stiffness and pushability, features which are important when maneuvering balloon catheters along tortuous and/or partially occluded blood vessels. Despite a number of different OTW balloon catheter systems currently known in the art, there is a continuous need for a system that can more efficiently and safely collect plaque debris and other particulate matter from the lumen of internal body passages such as pathologically-involved blood vessels.

US published patent application No. 2007/0083158 incorporated herein by reference in its entirety, describes an OVT balloon catheter system having an intussuscepting balloon and including a pressure regulating mechanism for preventing pressure changes within the catheter and the balloon using an overpressure valve for releasing inflation fluid upon pressure increases over a pressure threshold or by using a syringe-like part formed in the catheter outer conduit to accommodate the fluid ejected from the balloon during intussuscepting of the balloon. The operator of the catheters described in US published patent application No. 2007/0083158 may monitor the degree of proximal pulling of the inner conduit of the catheter by monitoring a scale provided on the inner conduit of the catheter while pulling the inner conduit proximally to cause intussuscepting of the catheter's balloon. While this may enable the operator to assess the degree of movement of the inner conduit within the outer conduit, such monitoring may require time and attention of the operator which may unnecessary increase the time required for the procedure, and may also result in operator error in reading the scale. It would therefore be advantageous to enable the operator to perform all the necessary steps for operating the catheter without having to pay attention to any scale while still ensuring that the balloon is not accidentally damaged by excessive pulling of the inner conduit in the proximal direction.

In the catheters described in US published patent application No. 2007/0083158, if the length of the balloon or the crossing (inflated) diameter of the balloon changes, the entire syringe-like structure will need to be matched to the dimensions of the balloon in order to ensure that a sufficient amount of inflation fluid is accommodated by the syringe like structure during intussuscepting of the balloon. This fact may necessitate the production and stocking of a large number of different catheter parts for producing catheters with different balloon dimensions. This may be undesirable from a cost and logistical point of view and may involve increased cost of manufacturing, assembling and stocking of such catheters and/or catheter parts. Additionally, from the operational point of view, the necessary variations in the length and/or diameter of the syringe-like structure needed for different lengths and/or different diameters of balloons may result is substantial variations in the catheter system size and dimensions which may cause confusion and necessitate longer training of medical personnel.

Furthermore, the catheters described in US published patent application No. 2007/0083158, disclose the use of a safety lock for preventing axial movements of the inner conduit within the outer conduit. The safety lock comprises a u-shaped gripping clip for gripping the inner tube. A part of the safety lock 14 penetrates the wall of the outer conduit of the catheter through a tight orifice formed in the outer conduit of the catheter. Such an arrangement is relatively cumbersome to implement and test because it necessitates the use of sealing gaskets for rendering the orifice fluid tight and may leak inflation fluid and/or cause reduction of the pressure within the balloon during the inflation of the balloon. Furthermore, under certain circumstances, if the safety lock is in the locked position such that the u-shaped gripping clip is gripping the inner tube, the inner tube may still be moved distally within the outer conduit if a force accidentally applied the inner conduit by the operator overcomes the friction by the gripping clip and the inner conduit, which may result in ejection of captured debris from the intussuscepted balloon into the body passage or blood vessel.

US published patent application No. 2009/0204069 incorporated herein by reference in its entirety, discloses rapid exchange (RE) catheters having intussuscepting balloons with pressure regulating mechanisms similar to those used in the OVT catheters of published US patent application No. 2007/0083158.

SUMMARY OF THE INVENTION

There is therefore provided, in accordance with an embodiment of the balloon catheter systems of the present application, a balloon catheter system having an intussuscepting balloon. The catheter system includes an outer conduit and an inner conduit suitable for passage over a guide wire. The inner conduit is disposed within the lumen of the outer conduit such that the longitudinal axes of the inner and outer conduits are substantially parallel. The inner conduit is positioned such that the distal tip thereof extends beyond the distal tip of the outer conduit. The inner conduit is adapted for being moved along its longitudinal axis in relation to outer conduit. The catheter system also includes an inflatable balloon having a balloon diameter and a balloon length. The proximal margin of the balloon is sealingly attached to the outer surface of the distal tip of the outer conduit and the distal margin of the balloon is sealingly attached to the outer surface of the portion of the inner conduit that extends beyond the distal tip of the outer conduit. The distal end portion of the balloon is adapted for intussuscepting upon proximal movement of the inner conduit in relation to the outer conduit. The catheter system also includes a handle adapted for moving the inner conduit proximally within the outer conduit and for removing a volume of an inflation fluid from the balloon into an expandable chamber of the handle when the balloon is being intussuscepted in an inflated state, such that during the intussuscepting of the balloon the pressure within the balloon and the expandable chamber remains substantially unchanged. The handle includes a housing and a hollow fluidic system disposed within the housing. The fluidic system includes a first end sealingly attached to the outer conduit and a second end sealingly attached to a hollow drawing member. The fluidic system also includes a fluidically sealable fluid port for introducing inflating fluid into the balloon through a space formed between the inner conduit and the outer conduit and for withdrawing inflating fluid from the balloon through the fluidic system. The handle also includes a hollow plunger assembly movably disposed in the housing. The plunger assembly has a part thereof sealingly and movably disposed within the hollow drawing member to form the expandable chamber. The inner conduit is attached to the plunger assembly. The plunger assembly is adapted to be partially pulled out of the housing to longitudinally proximally move the inner conduit within the outer conduit for intussuscepting the balloon and to expand the expandable chamber for accommodating inflating fluid ejected from the balloon during the intussuscepting thereof. The handle also includes a locking mechanism movably disposed within the housing for controllably enabling and disabling the moving of the inner conduit within the outer conduit and the moving of the plunger assembly within the hollow drawing member. The maximal longitudinal proximal moving distance of the plunger assembly within the hollow drawing member is equal to or shorter than the balloon length and the inner cross-sectional area of the hollow drawing member is matched to the balloon diameter.

There is also provided, in accordance with an embodiment of the handles of the present application, a handle for use in a balloon catheter system having an intussuscepting balloon. The catheter system includes an outer conduit and an inner conduit suitable for passage over a guide wire. The inner conduit is disposed within the lumen of the outer conduit such that the longitudinal axes of the inner and outer conduits are substantially parallel. The inner conduit is positioned such that the distal tip of the inner conduit extends beyond the distal tip of the outer conduit. The inner conduit is adapted for being moved along its longitudinal axis in relation to the outer conduit. The catheter system includes an inflatable balloon having a balloon diameter and a balloon length. The proximal margin of the balloon is sealingly attached to the outer surface of the distal tip of the outer conduit and the distal margin of the balloon is sealingly attached to the outer surface of the portion of the inner conduit that extends beyond the distal tip of the outer conduit. The distal end portion of the balloon is adapted for intussuscepting upon proximal movement of the inner conduit in relation to the outer conduit. The handle includes a housing and a hollow fluidic system disposed within the housing. The fluidic system includes a first end sealingly attachable to the outer conduit and a second end sealingly attached to a hollow drawing member. The fluidic system also includes a fluidically sealable fluid port for introducing inflating fluid into the balloon through a space formed between the inner conduit and the outer conduit and for withdrawing the inflating fluid from the balloon through the fluidic system. The handle also includes a hollow plunger assembly movably disposed in the housing. The plunger assembly has a part thereof sealingly and movably disposed within the hollow drawing member to form an expandable chamber. The inner conduit is attached to the plunger assembly. The plunger assembly is adapted to be partially pulled out of the housing to longitudinally proximally move the inner conduit within the outer conduit for intussuscepting the balloon and to expand the expandable chamber for accommodating inflating fluid ejected from the balloon during the intussuscepting thereof. The handle also includes a locking mechanism movably disposed within the housing for controllably enabling and disabling the moving of the inner conduit within the outer conduit and the moving of the plunger assembly within the hollow drawing member. The maximal longitudinal proximal moving distance of the plunger assembly within the hollow drawing member is equal to or shorter than the balloon length and the inner cross-sectional area of the hollow drawing member is matched to the balloon diameter.

Furthermore, in accordance with an embodiment of the system and the handle of the present application, the locking mechanism includes at lease one elongated member having at least one stopping member. The at least one stopping member is positioned on the at least one elongated member to engage with at least one stopping member disposed at the proximal end of the housing such that the proximal moving of the plunger assembly is stopped at the maximal longitudinal proximal moving distance.

Furthermore, in accordance with an embodiment of the system and the handle of the present application, the locking mechanism includes at least a first locking member disposed at the proximal end of the at least one elongated member. The first locking member is adapted to prevent the locking mechanism from being proximally pulled out of the housing by being locked within a locking slot formed in the housing.

Furthermore, in accordance with an embodiment of the system and the handle of the present application, the locking mechanism also includes at least a second locking member disposed at the distal end of the at least one elongated member and spaced apart from the first locking member. The second locking member is adapted to prevent the locking mechanism from being distally pushed inside the housing when the second locking member is locked within the locking slot.

Furthermore, in accordance with an embodiment of the system and the handle of the present application, the locking mechanism includes at least one releasing member operable to allow the locking mechanism and the plunger assembly to be proximally pulled away from the housing.

Furthermore, in accordance with an embodiment of the system and the handle of the present application, the locking mechanism is selected from a singe pronged locking mechanism including one elongated member and a double pronged locking mechanism including two elongated members.

Furthermore, in accordance with an embodiment of the system and the handle of the present application, the locking mechanism is a double pronged locking mechanism including two elongated members flanking at least a portion of the plunger assembly.

Furthermore, in accordance with an embodiment of the system and the handle of the present application, the plunger assembly includes a hollow plunger rod and a gasket attached to the plunger rod. The gasket is adapted to slidably and sealingly move inside the hollow drawing member to change the volume of the expandable chamber.

Furthermore, in accordance with an embodiment of the system and the handle of the present application, the hollow fluidic system includes a hollow three-way connector.

Furthermore, in accordance with an embodiment of the system and the handle of the present application, the hollow three-way connector is shaped as a T-connector.

Furthermore, in accordance with an embodiment of the system and the handle of the present application, the hollow drawing member is a cylindrical tube sealingly attached within the proximal end of the three way connector.

Furthermore, in accordance with an embodiment of the system and the handle of the present application, the system includes a pulling knob attached to the locking mechanism and to the proximal end of the plunger assembly for assisting the pulling and pushing of the locking mechanism and the plunger assembly.

Furthermore, in accordance with an embodiment of the system and the handle of the present application, the catheter system also includes a locking mechanism stabilizing member immovably disposed within the housing for stabilizing the movement of the locking mechanism within the housing.

Furthermore, in accordance with an embodiment of the system and the handle of the present application, the locking mechanism stabilizing member has a hollow passage formed therein for stabilizing the movement of a hollow plunger rod included in the plunger assembly. The plunger rod is movably disposed within the hollow passage of the stabilizing member.

Furthermore, in accordance with an embodiment of the system and the handle of the present application, the housing includes a first housing half and a second housing half.

Furthermore, in accordance with an embodiment of the system and the handle of the present application, the housing also includes a nose piece for connecting the distal ends of the first housing half and the second housing half together and a collar for connecting the proximal ends of said first housing half and a second housing half together.

Furthermore, in accordance with an embodiment of the system and the handle of the present application, the handle includes a pulling knob attached to the plunger assembly.

Furthermore, in accordance with an embodiment of the system and the handle of the present application, the pulling knob includes a first pulling knob half and a second pulling knob half.

Furthermore, in accordance with an embodiment of the system and the handle of the present application, the distal parts of the locking mechanism and of the plunger assembly are attached to the pulling knob.

There is also provided, in accordance with an embodiment of the methods of the present application, a method for assembling an intussuscepting balloon catheter system having a desired balloon length and balloon diameter. The method includes the steps of: providing a plurality of standard catheter system components, said plurality of standard components includes at least a housing, a plunger rod, a three-way hollow connector and a pulling knob, selecting an inflatable balloon having a desired length and diameter, the balloon is sealingly attached to an outer conduit at its proximal end and to an inner conduit at its distal end, the inner conduit is movably disposed within the outer conduit, providing a plurality of non-standard components of the catheter system and selecting from the plurality of non-standard components a locking mechanism constructed to match the length of the selected balloon, a hollow drawing member having an inner diameter matching the diameter of the balloon, a plunger gasket having an outer gasket diameter matching the inner diameter of the hollow drawing member, to match the length and the diameter of the balloon selected in said step of selecting, and assembling the standard components, the selected balloon, the selected locking mechanism, the hollow drawing member, and the selected plunger gasket to form the catheter system.

Furthermore, in accordance with an embodiment of the methods of the present application, the locking mechanism includes at least one elongated member having one or more stopping members therealong configured to engage with one or more housing stopping members formed in the housing of the catheter system and said step of providing a plurality of non standard components includes selecting a locking mechanism having the stopping members disposed at a position along the at least one elongated member such that when the locking mechanism is proximally moved within the housing, the stopping members engage with the one or more housing stopping members after traveling a drawing distance L substantially equal to or smaller than the length of the balloon selected in the step of selecting.

Finally, in accordance with an embodiment of the methods of the present application, the hollow drawing member includes a cylindrical hollow tube having a lumen with a lumen diameter. The plunger gasket has a diameter adapted to sealingly and movably fit within the lumen of the cylindrical hollow tube, and the step of providing a plurality of non standard components includes selecting a cylindrical hollow tube having a lumen diameter and a matching plunger gasket diameter from the plurality of the non-standard components such that when the locking mechanism is proximally moved within the housing of the standard components, the amount of an inflation fluid ejected from the selected balloon at any stage of the moving of the locking mechanism is accommodated within the lumen of the hollow drawing the said catheter system.

BRIEF DESCRIPTION OF THE DRAWINGS

The present invention is illustrated by way of example in the figures of the accompanying drawings, in which like references indicate similar elements and in which:

FIGS. 8A-8B are schematic isometric view and a top view, respectively, illustrating some of the components of the balloon catheter system of FIG. 1, after full proximal retraction of the plunger rod, in accordance with an embodiment of the of the catheter systems of the present application;

DETAILED DESCRIPTION OF THE INVENTION

Figure 1:
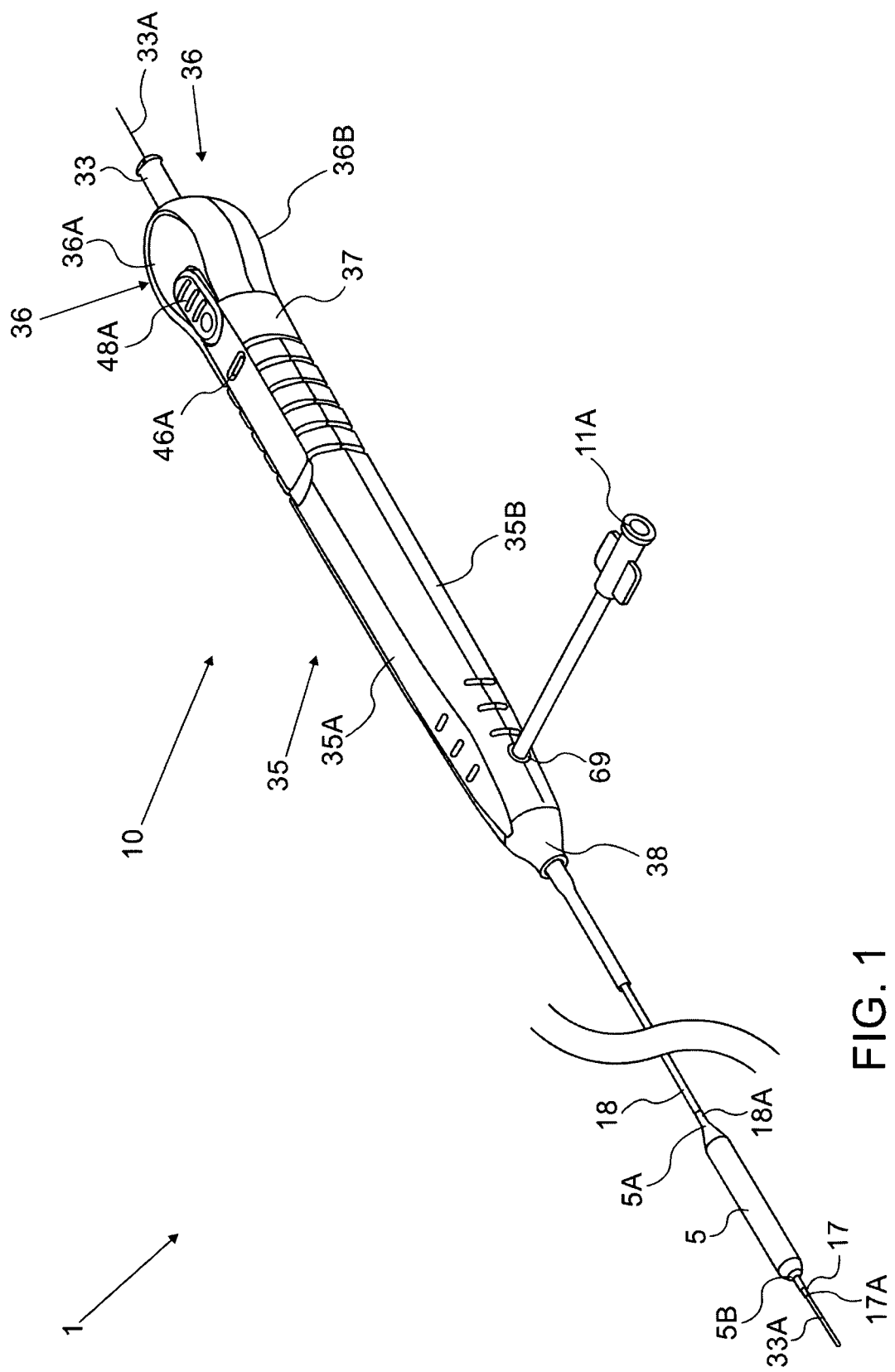
FIG. 1 is a schematic isometric view, illustrating an exemplary balloon catheter system, in accordance with an embodiment of the catheters of the present application.

In accordance with an aspect of an embodiment of the present disclosure, the system includes a handle adapted to proximally move the inner conduit relative to the outer conduit, the handle is further adapted to accommodate a volume of an inflation fluid ejected from the balloon into an expandable chamber in the handle during intussuscepting of the balloon when the balloon is in an inflated state. During intussuscepting of the balloon the pressure within the balloon and the expandable chamber remains substantially unchanged.

In accordance with an aspect of an embodiment of the present disclosure, the expandable chamber includes a plunger assembly sealingly and movingly disposed within a hollow drawing member. The inner conduit of the catheter is attached to the plunger assembly such that, when the plunger is proximally drawn within the hollow drawing member, the inner conduit is longitudinally proximally moved relatively to the outer conduit for intussuscepting the balloon. A maximum longitudinal proximal moving distance (drawing distance) of the plunger assembly within the hollow drawing member may be equal to or shorter than a length of the balloon, and optionally, an inner cross-sectional area of the hollow drawing member is matched to an inflated diameter of the balloon. The drawing distance and (optionally) the inner cross-sectional area are configured such that substantially all the inflation fluid ejected from the balloon is drawn into the hollow drawing member when the inner conduit is pulled over the drawing distance. As a result, there is no substantial inflation fluid pressure change during intussuscepting of the balloon.

In accordance with an aspect of some embodiments of the present disclosure, the handle includes a locking mechanism adapted to control the drawing distance over which the plunger assembly is proximally pulled inside the hollow drawing member. Optionally, the locking mechanism is adapted to prevent the plunger assembly from being unintentionally or accidentally drawn. Optionally, the locking mechanism is adapted to prevent the plunger assembly from being unintentionally or accidentally distally pushed into the hollow drawing member after completion of intussuscepting of the balloon. An Additional advantage of the locking mechanism is that it is constructed to enable safely and positively locking of the locking mechanism within the catheter's handle and preventing or reducing the possibility of unintentional or accidental axial moving of the inner conduit within the outer conduit of the catheter. This is advantageously implemented without any part or component of the locking mechanism penetrating and passing through the wall of the outer conduit. This reduces the possibility of any leaks from the outer conduit by eliminating the need for gaskets in the safety locking mechanism and improves the safety of the operation of the catheter system.

In accordance with an aspect of some embodiments of catheter system, the catheter system may be adapted for use with balloons of different lengths and/or different inflated diameters. The only parameters in the handle which vary for different lengths and/or diameters of the balloon, are the drawing distance of the plunger assembly and optionally the inner cross-sectional area (or inner diameter) of the hollow drawing member. This feature is advantageous as most of the components in the handle remain the same and do not require changing regardless of the size (length and/or inflated diameter) of the balloon. In this embodiment, the only components requiring change for constructing catheters having different sizes of balloon are the hollow drawing member (length and/or inner cross-sectional area may be changed), a gasket included in the plunger assembly adapted to match the inner cross-sectional area of the hollow drawing member, and/or a locking mechanism adapted to control the drawing distance of proximal pulling of the assembly. Optionally, the change in the hollow drawing member includes maintaining an outer cross-sectional area of the hollow drawing member while varying the inner cross-sectional area. Optionally, both the inner and outer cross-sectional areas are varied.

An advantage of the balloon system described hereinafter is that a plurality of balloon catheter systems having different balloon sizes may be readily manufactured, the systems requiring minimal component changes during their manufacture. Additionally, a cost of manufacturing such a plurality of systems with different balloon sizes is substantially reduced and made more efficient as a required stock of different parts is greatly reduced.

Another advantage is that a graduated scale as previously disclosed in US Patent Publication No. 2007/0083158 becomes redundant, and relieves an operator (for example, a physician) from the need to use such a scale. The balloon catheter system may be preset by a manufacturer of the system (by assembling the necessary parts) such that when the plunger assembly is pulled proximally by a predetermined maximal drawing distance the balloon is properly intussuscepted. Additionally (and optionally), once the plunger has been proximally pulled to the preset distance suitable for achieving full (or optionally partial) intussuscepting of the balloon, the locking mechanism is locked into place such that it cannot be further moved axially (either proximally or distally) without a set of intentional and coordinated actions performed by the operator. This feature increases the safety of the interventional procedure by eliminating the use of human judgment during intussuscepting, reducing a possibility of physician error and avoiding unintentional reversal of the intussuscepting of the balloon while the balloon is still within the body. Furthermore, the procedure is standardized and is greatly simplified as far as the physician is concerned.

Moreover, by proper design of the length and dimensions of the handle, the plunger and the hollow drawing member, it is possible to manufacture a series of catheters with balloons having a common balloon diameter but different balloon length, while changing only a limited number of key components while the other catheter components remain unchanged.

Furthermore, by proper design of the length and dimensions of the handle, the plunger and the hollow drawing member, it is possible to manufacture a series of catheters with balloons having a common balloon length but different balloon diameters, while changing only a limited number of key components while the other catheter components remain unchanged.

Furthermore, by proper design of the length and dimensions of the handle, the plunger and the hollow drawing member, it is possible to manufacture a series of catheters with balloons having different balloon lengths and different balloon diameters, while changing only a limited number of key components while the other catheter components remain unchanged.

The method of keeping the overall catheter system dimensions and shape unchanged while permitting the system to be constructed and operated with balloons having a variety of lengths and diameters advantageously reduces the number of different parts that need to be manufactured and stocked, greatly streamlines production and enables significant cost saving in manufacturing cost the catheters due to reducing inventory. Also advantageous is the ability of providing an entire range of balloon dimensions which are being operated by a handle system having the same dimensions and mode of operation as this greatly facilitates and simplifies operator training and significantly shortens the learning curve.

Reference is now made to FIG. 1 is a schematic isometric view, illustrating an exemplary balloon catheter system, in accordance with an embodiment of the catheters of the present application. Balloon catheter system 1 includes a handle 10, an outer conduit 18 including a distal tip 18A, an inner conduit 17 including a distal tip 17A slidably disposed within the outer conduit and an inflatable balloon 5 sealingly attached at a proximal margin 5A to the outer conduit 18, and sealingly attached at a distal margin 5B to the inner conduit. The balloon catheter system 1, which may be but is not limited to, an OTW balloon catheter system, is adapted to remove objects such as, for example atheromatous plaque debris, or to collect samples from a body passageway such as a blood vessel. The balloon catheter system 1 may be further used to expand a region of a body passageway, such as for example an atheromatous narrowing or occlusion of a blood vessel (not shown), in addition to removing debris or other matter or objects therefrom. In accordance with an embodiment of the present application, balloon catheter system 1, while performing any one of, or any combination of, the above functions, is adapted to maintain a substantially constant pressure (unchanged pressure) inside the catheter system 1 and the balloon 5 during intussuscepting of balloon 5, upon proximal movement of the inner conduit 17 relative to the outer conduit 18.

The inner conduit 17 is suitable for passage over a guide wire (such as the guide wire 33A of FIG. 1). The inner conduit 17 is disposed within the lumen of the outer conduit 18 such that the longitudinal axes of the inner conduit 17 and of the outer conduit 18 are substantially parallel. The inner conduit 17 is positioned such that the distal tip of the inner conduit 17 extends beyond the distal tip of the outer conduit 18.

The inner conduit 17 may be moved along its longitudinal axis in relation to the outer conduit 18. The inflatable balloon 5 of the catheter system 1 has a balloon diameter D1 and a balloon length L1. The proximal margin of the balloon 5 is sealingly attached to the outer surface of the distal tip of the outer conduit 18 and the distal margin of the balloon 5 is sealingly attached to the outer surface of the portion of said inner conduit 17 that extends beyond the distal tip of the outer conduit 18. The distal end portion of the balloon 5 is adapted for intussuscepting upon proximal movement of the inner conduit 17 in relation to the outer conduit. The manner of the intussuscepting of the balloon 5, the materials, shapes and dimensions usable in the construction of the balloon 5, the inner conduit 17 and the outer conduit 18 are as described in detail in published US patent application No. 2007/0083158.

The handle 10 includes a housing 35 for packaging numerous components and assemblies functionally associated with operation of balloon system 1, and which are described further in detail on in relation to other figures. The housing 35 maybe made from any suitable engineering or structural plastic material or polymer based material, such as, but not limited to a suitable polycarbonate based plastic, but any other suitable material known in the art may be used. The housing 35 includes a first housing half 35A, a second housing half 35B, a nose piece 38 adapted to secure together the distal ends of the first and second housing halves 35A and 35B, respectively. The housing 35 also includes a collar 37 adapted to secure together the proximal ends of the first and second housing halves 35A and 35B, respectively. The housing 35 also includes a pulling knob 36 including a first pulling knob half 36A and a second pulling knob half 36B.

The pulling knob 36 is adapted to be longitudinally pulled in a proximal direction by an operator (for example, a physician) while pushing down on a releasing member 48A (while simultaneously pushing on a second releasing member on the side of lower housing half 35B, shown as 48B in FIG. 3 and FIGS. 5A-5C) forming part of a locking mechanism 40 (not shown in its entirety in FIG. 1 but shown in detail in FIGS. 5A-5C) as described in detail hereinafter. The simultaneous pushing down action (performed by the operator) on the releasing members 48A and 48B releases two protruding locking members 41A and 41B of the locking mechanism 40 from two locking slots 46A and 46B formed in the first housing half 35A and the second housing half 35B (see FIG. 3), such that the pulling knob 36 is released from a locked state and may be pulled proximally. The proximal pulling of the pulling knob 36 results in proximal movement of a locking mechanism 40 and a hollow plunger rod 30A which are both attached to or secured within the pulling knob 36 at their proximal ends (as shown in detail in FIGS. 2A and 8B, hereinbelow).

The handle 10 further includes an insertion port 33. The insertion port 33 which may be the opening of a standard Luer connector, or any other suitable standard or proprietary connector having an insertion opening as known in the art which Luer may be attached to the proximal end of the hollow plunger rod 30A (as shown in detail in FIGS. 8A-8B), or alternatively may be simply an opening formed in the proximal end of the hollow plunger rod 30A. The opening of the Luer connector or any other insertion port 33 being used, allows a guide wire 33A to be inserted into the inner conduit 17. The guide wire 33A is typically used in OVT balloon catheter systems to guide balloon 5 to the body location where the balloon is to be inflated or treatment is to be provided. Inflation of the balloon 5 is done by inserting an inflation fluid into a fluid port 11A forming part of a fluidic system 11 (shown in detail in FIGS. 2A-2C and 4A-4C) which connects to an annular space (lumen) formed between the outer conduit 18 and the inner conduit 17. The Fluid port 11A may also be used to remove the inflation fluid from balloon system 1 when balloon 5 is deflated (generally using a standard indeflator, not shown). The inflation port may be, but is not limited to, a female Luer type port or any other type of port suitable for connecting an indeflator device (not Shown) to the catheter system 1.

In a typical mode of operation, a physician or operator may inserts the guide wire 33A through an introducer sheath into the body and pushes the guide wire 33A into the desired treatment or debris collection site, The OVT catheter 1 is then inserted over the guide wire 33A by inserting the guide wire 33A into the lumen of the distal tip of the inner conduit 17 and advanced to the treatment target site. Once positioned at the correct location within the blood vessel, an inflation fluid is inserted into fluid port 11A under pressure, by using an indeflator or a syringe or any other suitable the like), and the balloon 5 is inflated to a required diameter within the blood vessel. Once the balloon 5 is inflated to the required diameter, the fluid port 11A is sealed by leaving the indeflator connected or by (optionally) closing a three way stopcock (not shown) connected between the indeflator or other inflating device and the fluid port 11A, thereby preventing the inflation fluid from escaping through the fluid valve. The physician then simultaneously presses on the releasing member 48A and on the second releasing member 48B to free the pulling knob 36, and proximally pulls the pulling knob 36 a predetermined distance until the pulling knob stops. The distance pulled (drawing distance, described in greater detail below) is predetermined by a manufacturer of the balloon catheter system 1 and is dependent on the length of balloon 5 (size of the balloon).

The proximal pulling of the pulling knob 36 causes distal tip 17A to move proximally along a longitudinal axis x (shown in FIG. 4C below) relative to outer conduit 18, properly fully (or alternatively partially) intussuscepting the balloon 5 when the pulling knob 36 stops. The indeflator (not shown) connected to the fluid port 11A (directly or, optionally, through the three way stopcock, as described hereinabove) is then used for deflating the balloon 5. The balloon catheter system 1 is then withdrawn from the body of the patient through the insertion sheath or other insertion opening together with any debris and/or particulate matter trapped in the intussuscepted balloon 5. The methods for using OVT and RE catheters with intussuscepting balloons for trapping and removing debris or secretions or particulate matter from the body and/or using the balloons to treat a diseased site and/or carry and deploy a stent, and/or operate as an anchoring device for inserting other treating devices into the treatment site are all disclosed in detail in published applications No. 2007/0083158 and 2009/0204069 and are therefore not described in detail hereinafter.

Figure 2A:
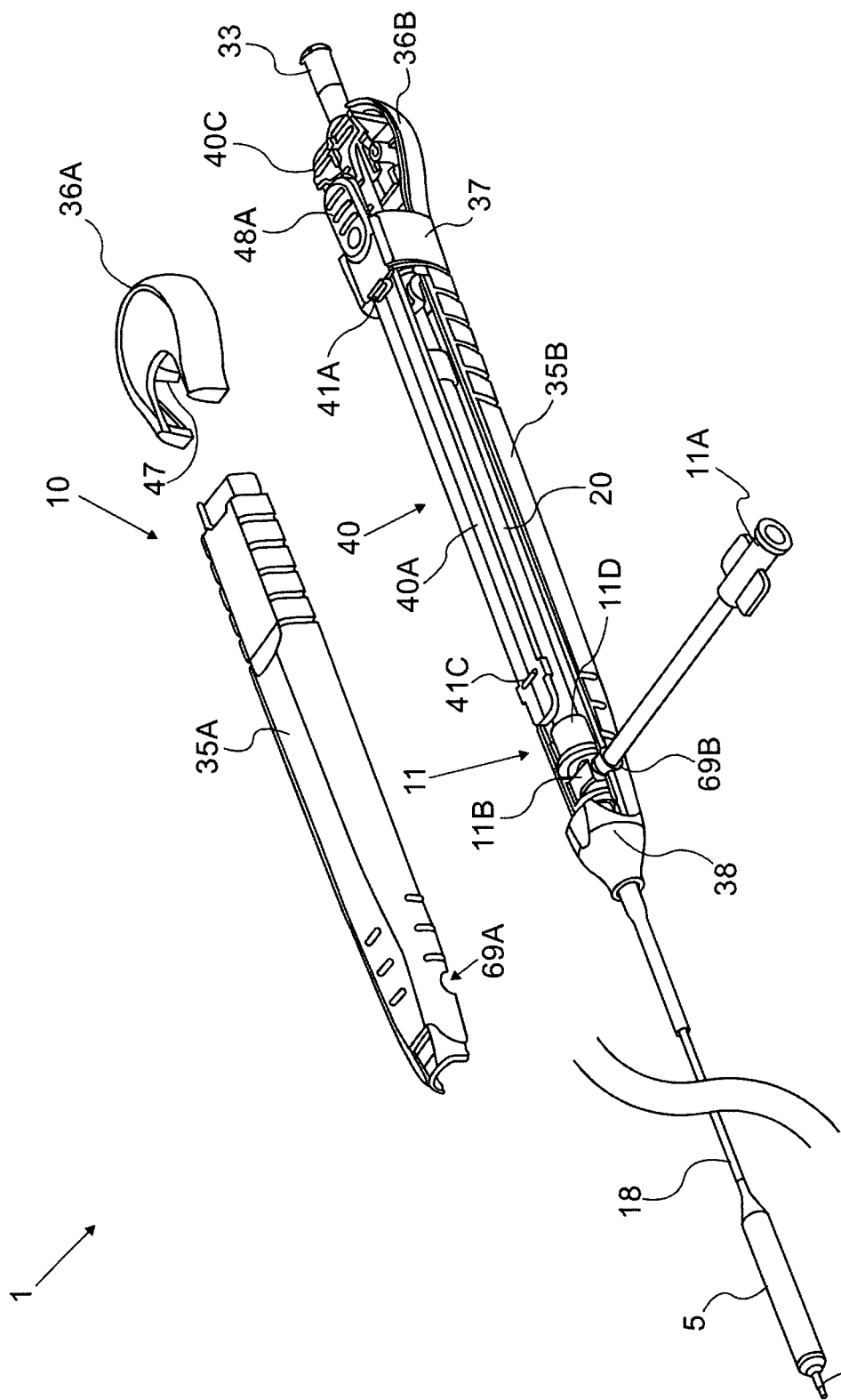
FIGS. 2A is schematic isometric view illustrating a handle of the balloon catheter system of FIG. 1 with a first housing half, and a pulling knob half removed, in accordance with an embodiment of the handle of the present application.
Figure 2B:
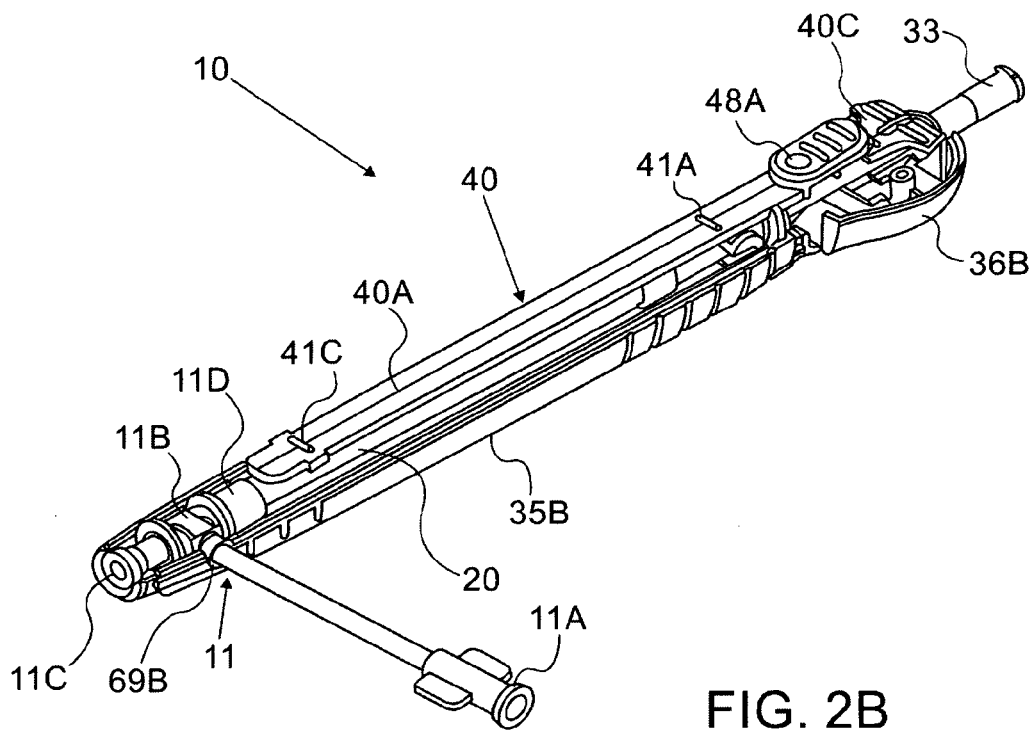
FIGS. 2B-2C are a schematic isometric view and a schematic top view, respectively, of part of the handle of FIG. 2A.
Figure 2C:
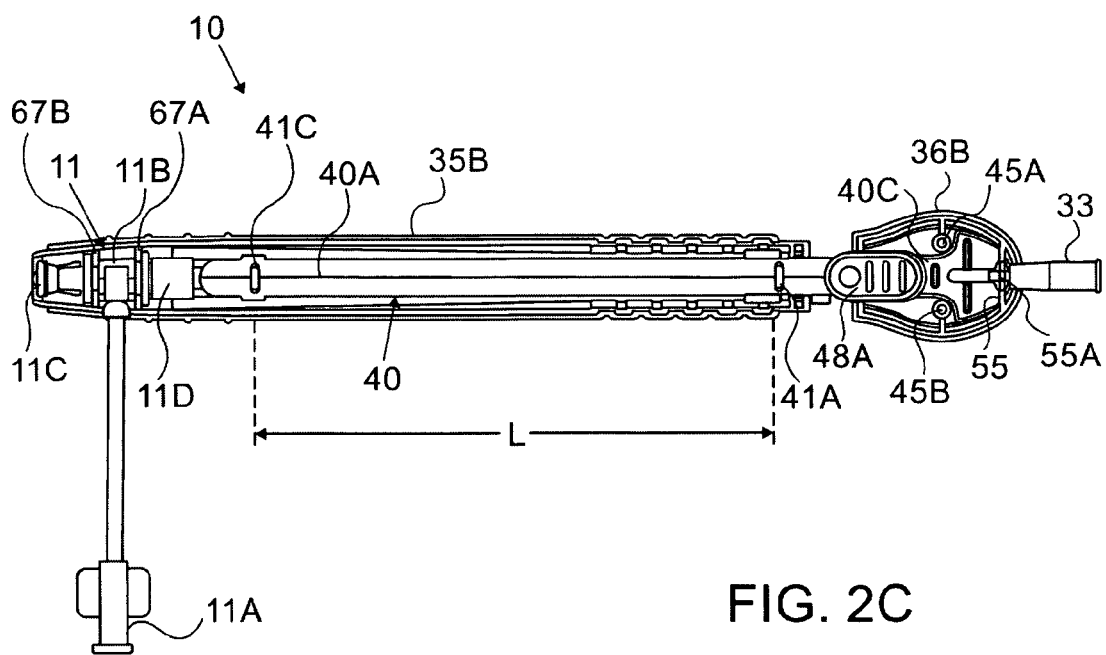

Reference is now made to FIGS. 2A-2C. FIG. 2A is schematic isometric view illustrating a handle of the balloon catheter system of FIG. 1 with the first housing half 35A, and a first pulling knob half 36A removed, in accordance with an embodiment of the handle of the present application. FIGS. 2B-2C are a schematic isometric view and a schematic top view, respectively, of part of the handle of FIG. 2A. In FIG. 2A, the first housing half 35A and the first pulling knob half 36A, are shown in an exploded configuration to disclose details of the internal components disposed within the handle 10 of the catheter system 1.

Disposed in the housing 35 is a fluidic system 11. The fluidic system 11 is adapted to allow an inflation fluid to be inserted through fluid port 11A into the lumen 25 (of FIG. 4C) formed between outer conduit 18 and inner conduit 17 for inflating the balloon 5. The fluidic system 11 is also adapted to allow inflation fluid to be drawn into and accommodated within a hollow drawing member 20 during the intussuscepting of the balloon 5. The fluidic system 11 includes a hollow three-way connector 11B, for example a T-connector, to which the fluid port 11A is sealingly attached. The three way connector 11B is sealingly attached to the proximal end 18B of the outer conduit 18 at a first end 11C thereof. The three way connector 11B is sealingly connected to a hollow drawing member 20 at an opposite second end 11D of the connector 11B. The hollow drawing member 20 may be implemented, as a hollow cylindrical draw tube. However, optionally, the hollow drawing member 20 may be also implemented as a hollow member having cross-sectional shapes other than circular, for example, oval, rectangular, triangular, or other polygonal shapes.

When the catheter system 1 is assembled, the three way connector 11B is disposed within the housing 35 such that two retaining members 67A and 67B formed in the distal part of the second housing half 35B are positioned within two spaced apart annular slots 27A and 27B, respectively formed within the three way connector 11B (as illustrated in FIGS. 4C and 4B and FIGS. 6A-C). A pair of similarly shaped retaining members (not shown) are formed in the distal end of the first housing half 35A and are also positioned within the annular slots 27A and 27B when the first housing half 35A is attached to the second housing half 35B to complete the housing 35. The fluid port 11A of the three way connector 11B passes through an opening 69 which is formed by two recesses 69A and 69B formed in the first housing half 35A and in the second housing half 35B, respectively when the housing halves 35A and 35B are assembled together to form the housing 35. This arrangement firmly fixes the three way connector 11B immovably within the assembled housing 35, as the retaining members 67A and 67B (as well as the opposing two retaining members of the first housing half 35A prevent any longitudinal or axial movement of the three way connector 11B within the housing 35 while the fluid port 11A prevents any rotational movements of the three way connector 11B because it is firmly held within the opening 69.

The locking mechanism 40 is movably disposed within the housing 35. The proximal side of the locking mechanism 40 is attached to or firmly secured within the pulling knob 36. The locking mechanism 40 is adapted to move longitudinally within housing 35 responsive to movement of pulling knob 36. In accordance with an embodiment of the catheter of the present application, the locking mechanism 40 is further adapted to restrict proximal pulling of the pulling knob 36 past the predetermined drawing distance during intussuscepting of the balloon 5 (as will be described in detail hereinafter). The locking mechanism 40 may include one or more safety features for preventing the physician from unintentionally or accidentally proximally pulling knob 36 away from housing 35 and/or from unintentionally or accidentally pushing the knob 36 distally into the housing 35 after intussuscepting of the balloon 5 is completed.

Figure 3:
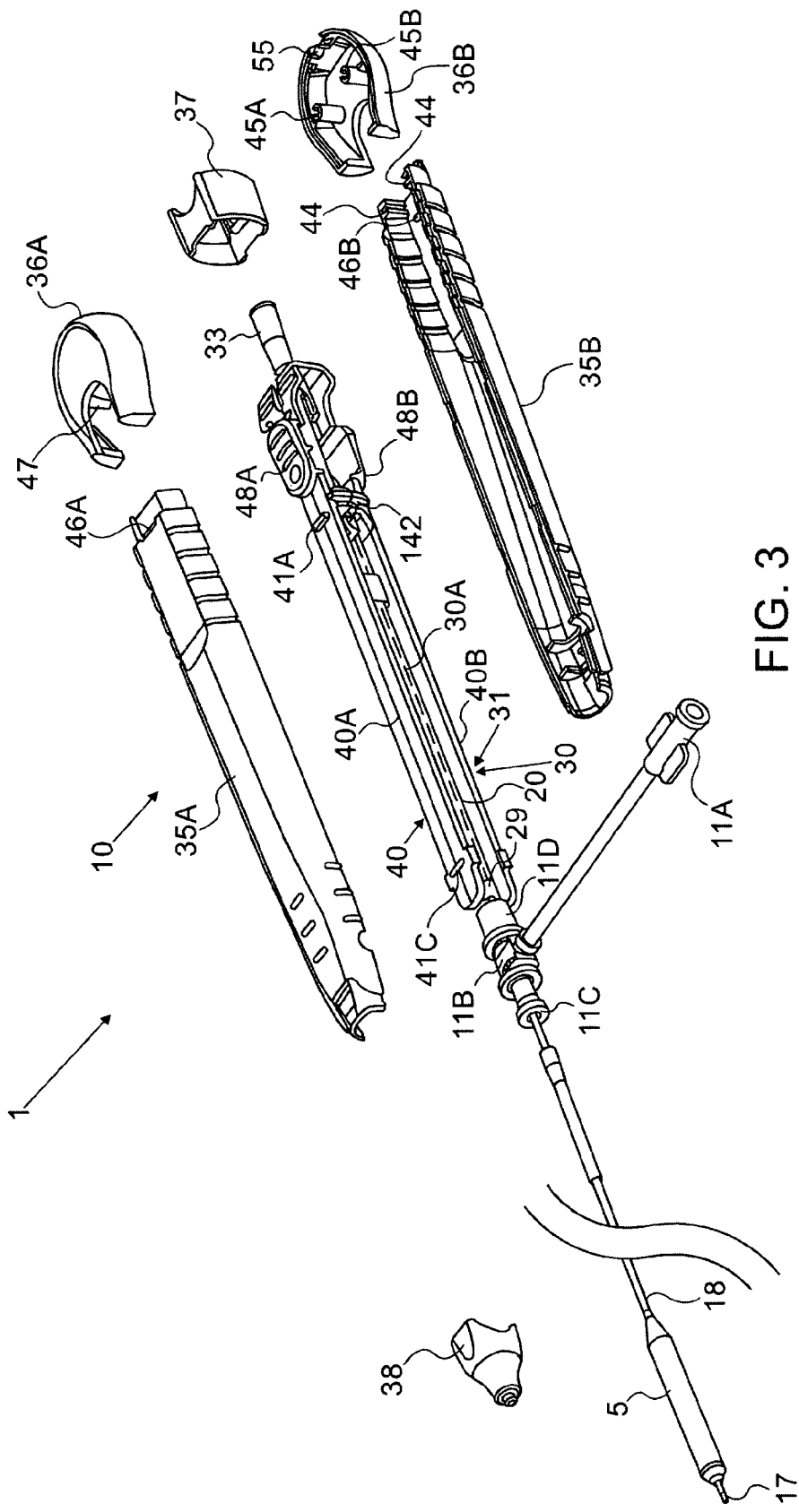
FIG. 3 is an isometric exploded view illustrating the balloon catheter system of FIG. 1 including the handle having an expandable chamber, in accordance with an embodiment of the catheter system of the present application.

In accordance with one embodiment of the catheters of the present application, the locking mechanism 40 is implemented as a double pronged locking member (double prong) including a first prong 40A and a second prong 40B (the second prong 40B is shown in FIG. 3 and in FIG. 5A-5C), the two prongs 40A and 40B are substantially parallel elongated members disposed longitudinally outside of and along the cylindrical draw tube 20 (the cylindrical draw tube 20 is positioned and disposed between the prongs 40A and 40B). A proximal end 40C of the double pronged locking mechanism 40 is disposed in and secured within the pulling knob 36 allowing the double pronged locking mechanism 40 to move together with the pulling knob 36. Securing of the proximal end 40C to the pulling knob 36 may be performed by two holding members 45A and 45B, which may be implemented as cylindrical hollow pins as shown in FIGS. 2B-2C. Alternatively or additionally, securing of the proximal end 40C may (optionally, but not obligatorily) include other means of attachment, such as but not limited to, fastening devices, screws, clips, nuts, bolts, and the like or by using a suitable glue or adhesive. Optionally, the pulling knob 36 may include more than two holding members (such as the holding member 45A and 45B), Furthermore, the holding members 45A and 45B may have other shapes different than cylindrical. Additionally or alternatively, holding members 45A and 45B are adapted to secure together the first pulling knob half 36A and the second pulling knob half 36B, by inserting and/or gluing thereinto two matching securing pins 47 forming part of the first pulling knob half 36A (it is noted that only one of the securing pins 47 may be seen in the isometric view of FIG. 2A). Proximal pulling of the pulling knob 36 (after simultaneous pushing down of the releasing members 48A and 48B of the locking mechanism 40) therefore moves the locking mechanism 40 and the hollow plunger rod 30A proximally and pulls them out of the housing 35. The proximal pulling of the hollow plunger rod 30A expands an expandable chamber 31 of the fluidic system 11 while causing the intussuscepting of the balloon 5, as is explained in detail hereinafter.

Figure 5A:
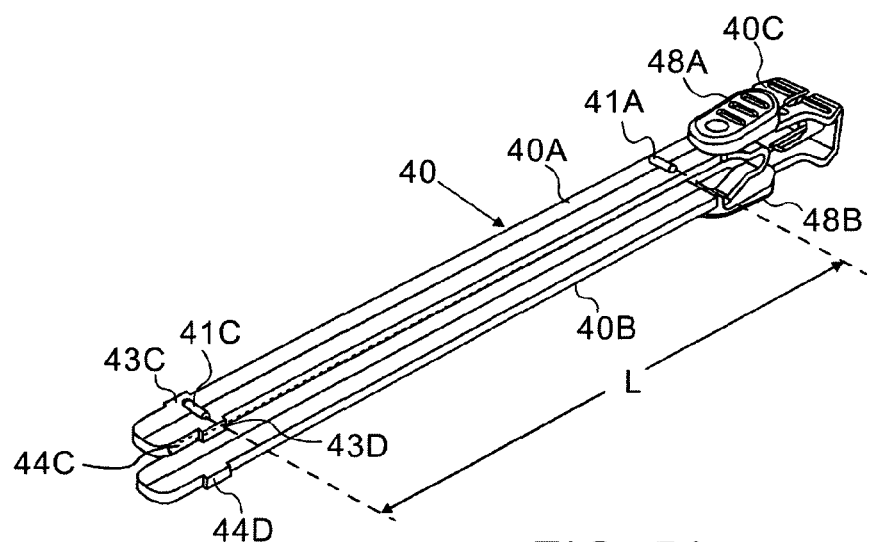
FIGS. 5A-5C are a schematic isometric view, a top view and a side view, respectively, of a safety locking mechanism of the handle of the balloon catheter system of FIG. 1, in accordance with an embodiment of the catheter systems of the present application.
Figure 5B:
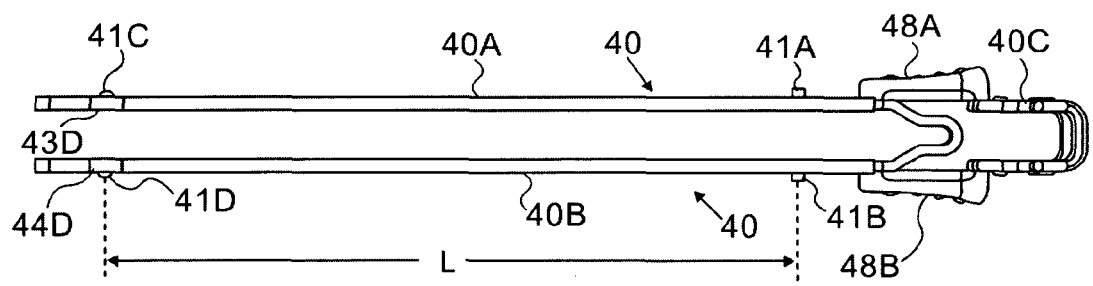
Figure 5C:
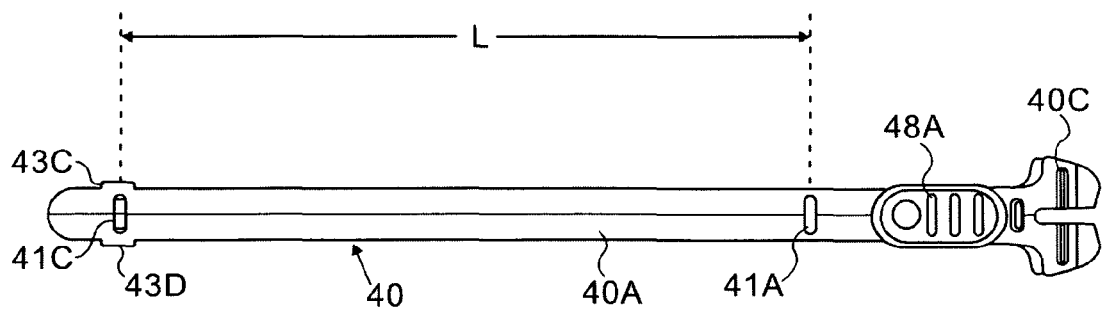

Among the safety features included in the double pronged locking mechanism 40 are protruding locking members 41A and 41C on prong 40A (and protruding locking members 41B and 41D on prong 40B as shown in FIGS. 5A-5C). The protruding locking members 41A and 41C (and the protruding locking members 41B and 41D of the prong 40B) are spaced apart by a drawing distance L, the protruding locking members 41A and 41C of the prong 40A are shaped to suitably fit into the locking slot 46A formed in the first housing half 35A, and the protruding locking members 41B and 41D of the prong 40B are shaped to suitably fit into locking slot 46B formed in the second housing half 35B (shown in FIG. 3). When the proximal locking members 41A and 41B are engaged in the locking slots 46A and 46B, respectively, the double pronged locking mechanism 40 and the pulling knob 36 which is attached thereto are immovably locked in place relative to housing 35 and cannot be axially moved (distally or proximally) within the housing 35. This safety feature prevents unintended or accidental proximal (or distal) moving of the pulling knob 36 and the attached double pronged locking mechanism 40.

Other safety features included in locking mechanism 40 include the releasing member 48A in prong 40A (and the releasing member 48B in prong 40B), which are in proximity to the proximal end 40C of the locking mechanism 40. The prongs 40A and 40B may be made from a suitable plastic or polymer based material such that they may flex or bend laterally (in a direction substantially orthogonal to the longitudinal axis x of the handle) in response to the operator pressing the releasing members 48A and 48B in a direction towards the longitudinal axis x of the handle 35. The bending or flexing of the prongs 40A and 40 B in response to inward pressure applied to the releasing members 48A and 48B by the fingers of the operator allows the protruding locking members 41A and 41B to move inwardly and to become disengaged from the locking slots 46A and 46B.

In order to disengage the locked pulling knob 36, the physician or operator simultaneously presses releasing members 48A and 48B causing the protruding locking members 41A and 41B to be released from their engagement within the locking slots 46A and 46B, respectively, allowing the pulling knob 36 to be pulled proximally and the double pronged locking mechanism 40 to slide proximally within the housing 35 over the drawing distance L. Sliding of the double prong locking mechanism 40 proximally over the drawing distance L eventually causes the distal locking member 41C and 41D to engage within the locking slots 46A and 46B, respectively, such that the double pronged locking mechanism 40 and the pulling knob 36 are immovably locked in place relative to the housing 35, preventing the pulling knob 36 and the double pronged locking mechanism 40 from being accidentally or unintentionally distally pushed into the housing 36. This safety feature prevents unintended or accidental distal pushing of the pulling knob 36 and the double pronged locking mechanism 40 which may result in undesirable release of trapped debris from the intussuscepted balloon 5.

Figure 4A:
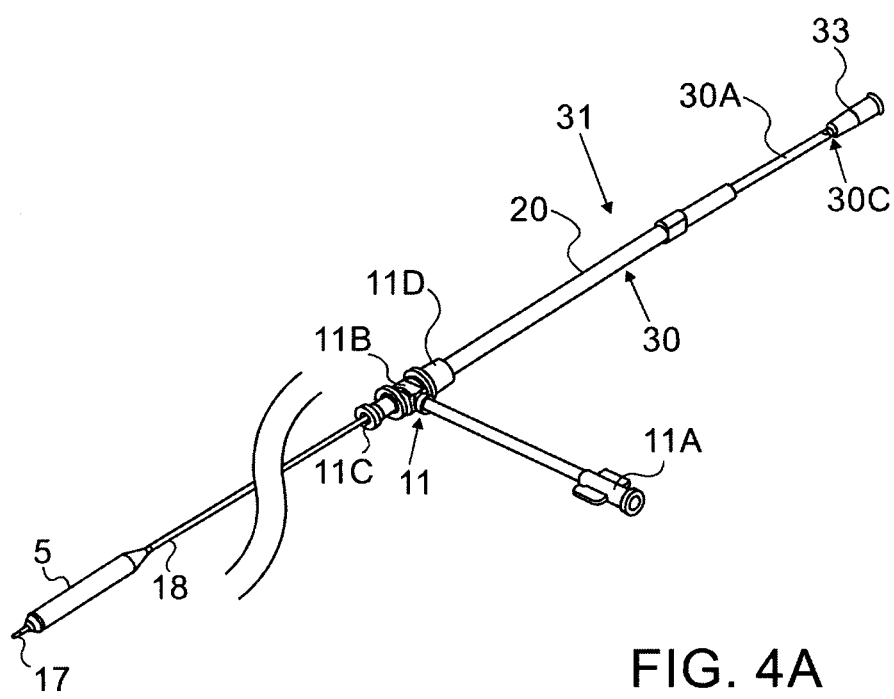
FIGS. 4A, 4B and 4C are a schematic isometric view, a schematic part-cross-sectional side-view and a schematic cross-sectional view, respectively, illustrating a fluidic system having an the expandable chamber suitable for use in the handle of the balloon catheter system of FIG. 1, in accordance with an embodiment of the catheter systems of the present application.
Figure 4B:
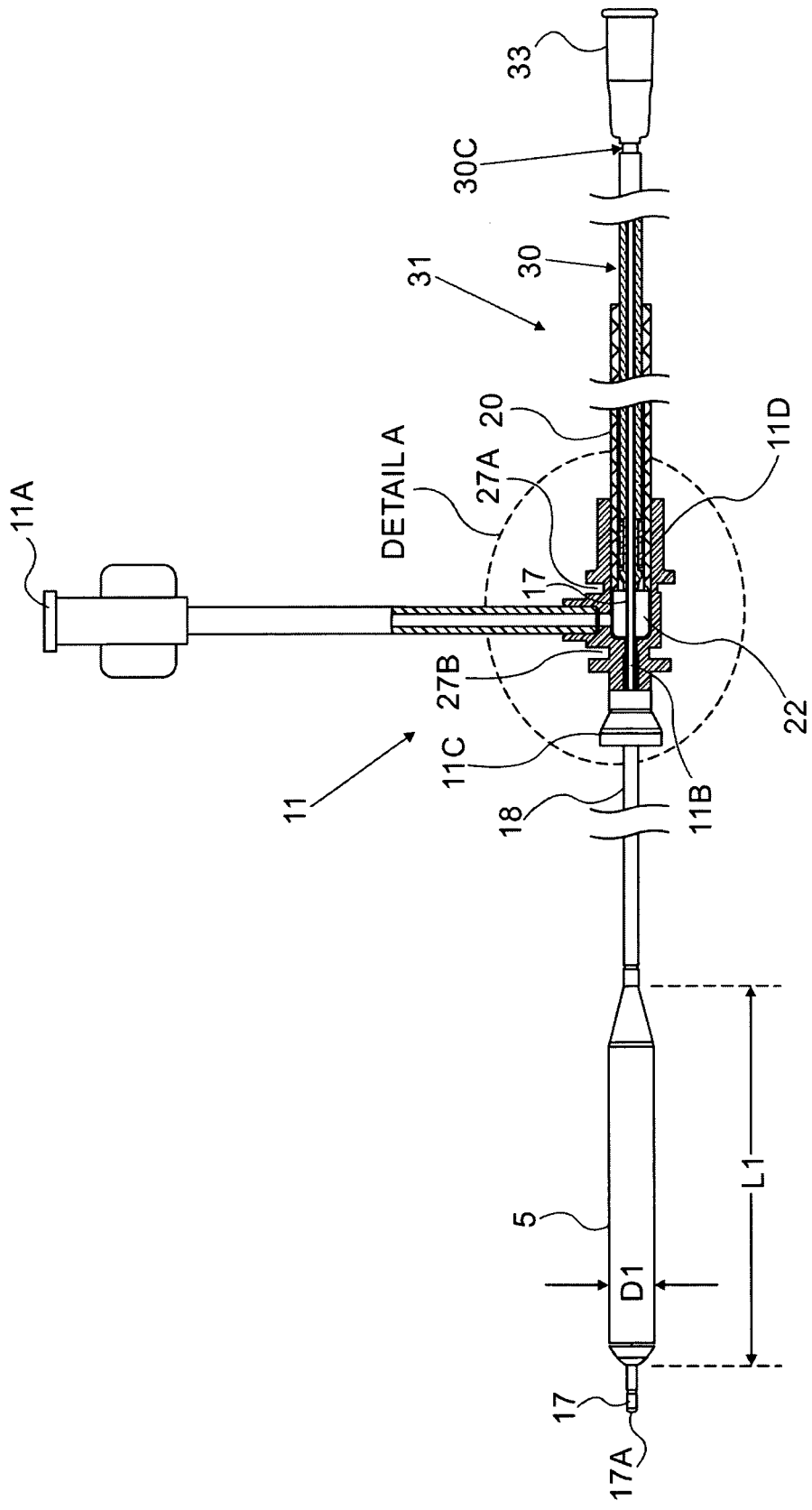
Figure 4C:
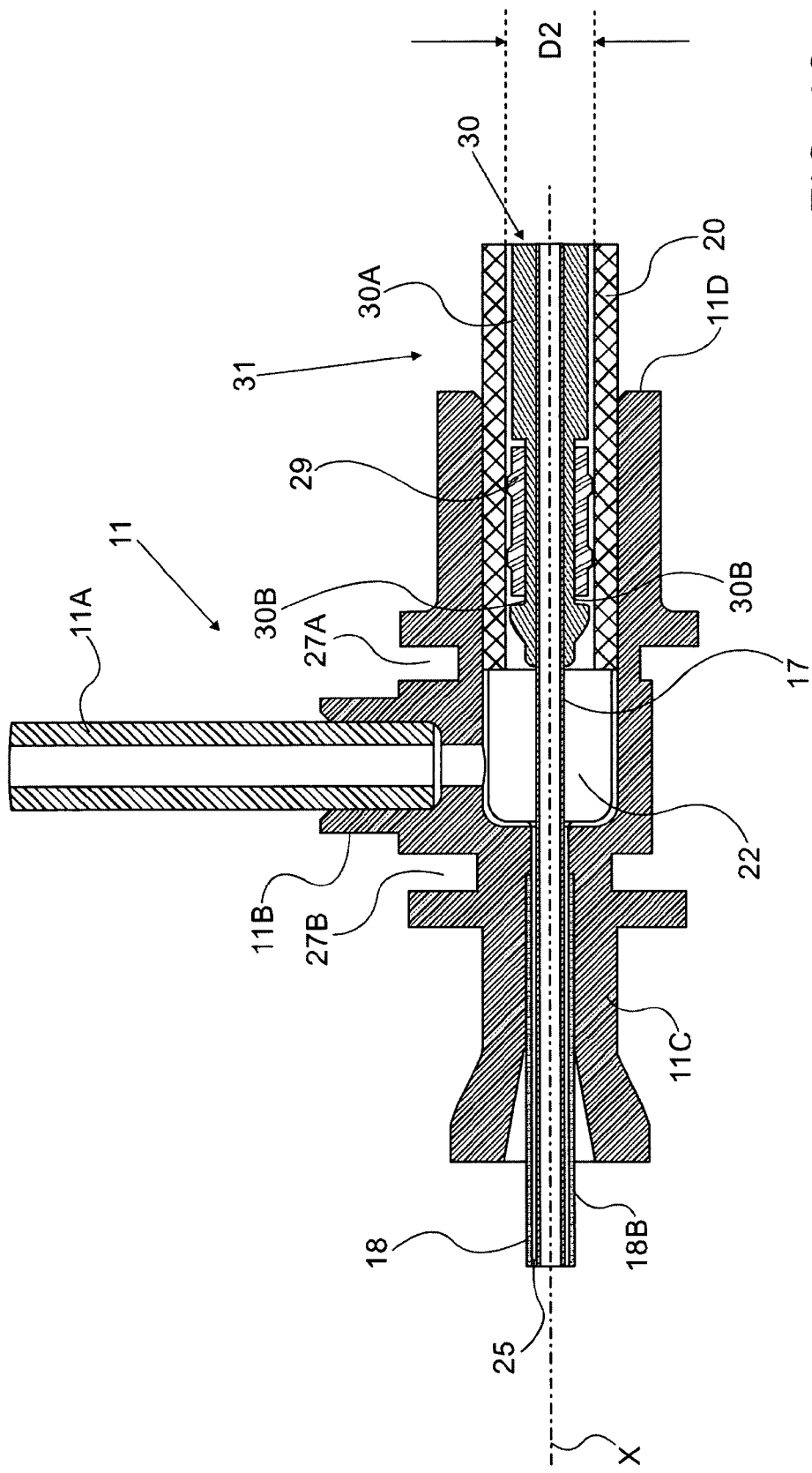
Figure 6A:
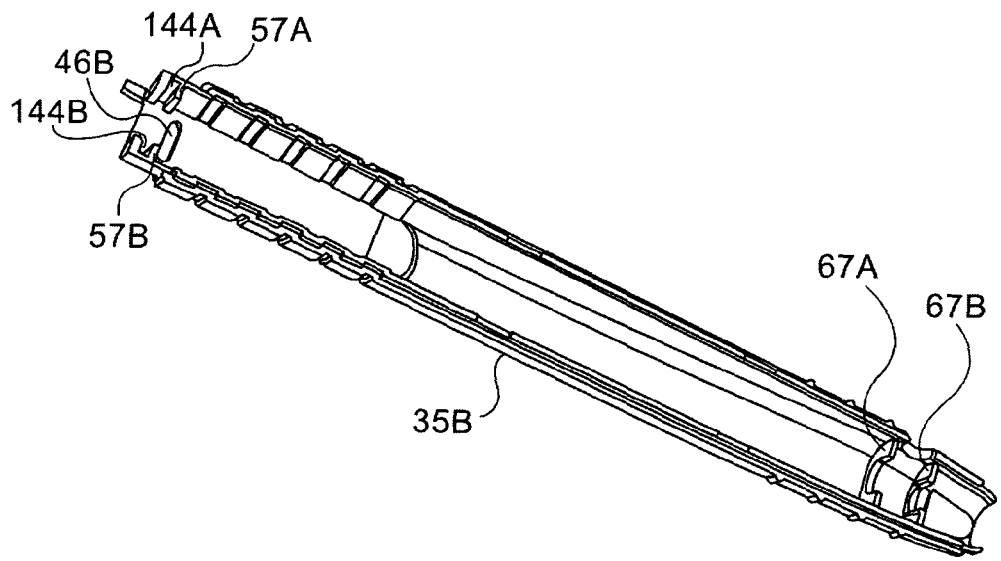
FIGS. 6A-6C are schematic isometric view, side view, and top view, respectively, illustrating a lower housing half in the handle of the balloon catheter system of FIG. 1, in accordance with an embodiment of the of the catheter systems of the present application.
Figure 6B:
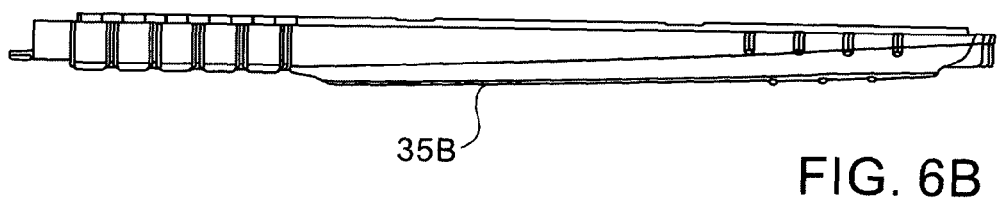
Figure 6C:
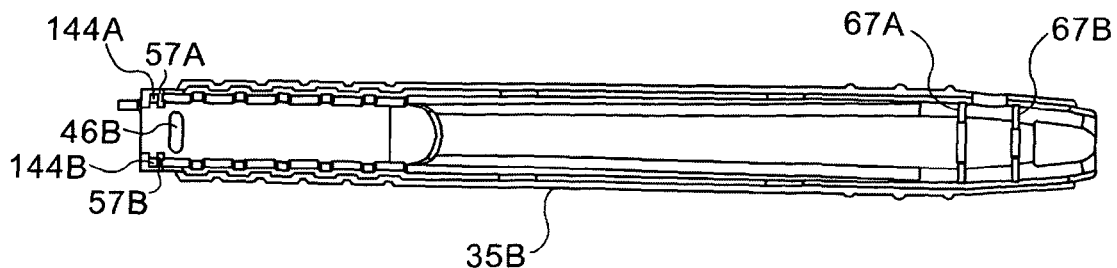
Figure 7A:
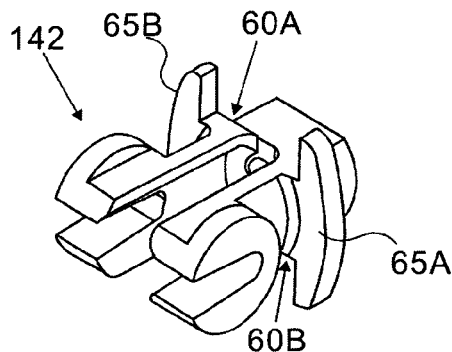
FIGS. 7A-7C are schematic isometric view, a side view, and a top view illustrating of a plunger rod guiding member of the handle of the balloon catheter system of FIG. 1, in accordance with an embodiment of the of the catheter systems of the present application.
Figure 7B:
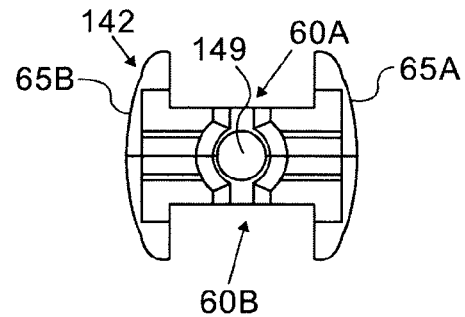
Figure 7C:
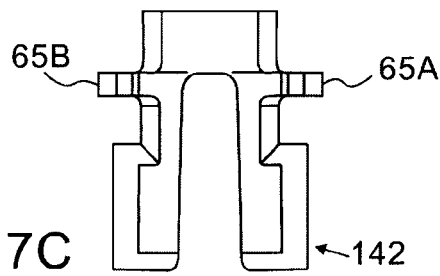
Figure 7D:
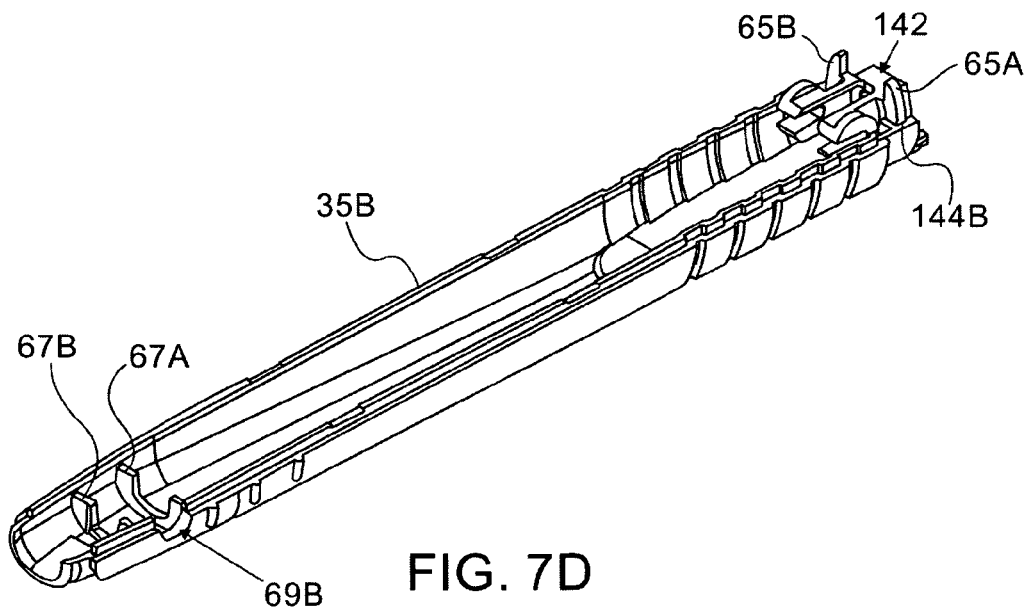
FIGS. 7D-7E are a schematic isometric view and a schematic top view, respectively, illustrating the lower housing half including the plunger rod guiding member, in the handle of the balloon catheter system of FIG. 1, in accordance with an embodiment of the of the catheter systems of the present application.
Figure 7E:
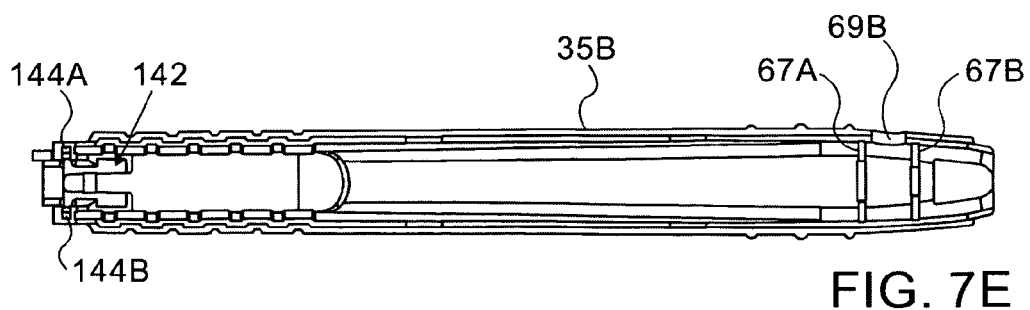

Reference is now made to FIGS. 3, 4A-4C, 5A-5C, 6A-6C and 7A-7D. FIG. 3 is an isometric exploded view illustrating the balloon catheter system of FIG. 1 including a handle having an expandable chamber, in accordance with an embodiment of the catheter system of the present application. FIGS. 4A, 4B and 4C are a schematic isometric view, a schematic part-cross-sectional side-view and a schematic cross-sectional view, respectively, illustrating a fluidic system having an the expandable chamber suitable for use in the handle of the balloon catheter system of FIG. 1, in accordance with an embodiment of the catheter systems of the present application. FIGS. 5A-5C are a schematic isometric view, a top view and a side view, respectively, of a safety locking mechanism of the handle of the balloon catheter system of FIG. 1, in accordance with an embodiment of the catheter systems of the present application. FIGS. 6A-6C are schematic isometric view, side view, and top view, respectively, illustrating a second housing half of the handle of the balloon catheter system of FIG. 1, in accordance with an embodiment of the of the catheter systems of the present application. FIGS. 7A-7C are schematic isometric view, a side view, and a top view illustrating of a plunger rod guiding member of the handle of the balloon catheter system of FIG. 1, in accordance with an embodiment of the of the catheter systems of the present application. FIGS. 7D-7E are a schematic isometric view and a schematic top view, respectively, illustrating the second housing half of the handle, including the plunger rod guiding member, in the handle of the balloon catheter system of FIG. 1, in accordance with an embodiment of the of the catheter systems of the present application.

The fluidic system 11 of the handle 10 includes an expandable chamber 31. The Expandable chamber includes a cavity 22 formed within the fluidic system 11 and an expandable (varying) part which comprises the volume formed within the drawtube 20 as the plunger assembly 30 is proximally moved. In accordance with an embodiment of the catheters of the present application, the expandable chamber 31 is formed by a plunger assembly 30 which is sealingly and movingly disposed inside the cylindrical draw tube 20. The expandable chamber 31 is adapted to maintain a substantially constant pressure (and to prevent over-pressure condition) within the balloon catheter system 1 and the lumen of the balloon 5 during the intussuscepting of the balloon 5. The plunger assembly 30 includes a hollow plunger rod 30A and a gasket 29. The hollow plunger rod 30A is made from a hollow stainless steel tube but any other strong materials may also be used. The gasket 29 may be made from rubber, latex, or a silicone based polymers or elastomers (but other suitable materials may also be used as is known in the art). Preferably (but not obligatorily), the gasket 29 is disposed in a suitable recess 30B formed in the hollow plunger rod 30A and is adapted to prevent inflation fluid from flowing into the cylindrical draw tube 20 while the balloon 5 is being inflated (or is already inflated, prior to intussuscepting). Alternatively, the gasket 29 may be disposed on, or attached to or glued to an outer surface of the hollow plunger rod 30A (if the hollow plunger rod does not include the recess 30B). The insertion port 33 is attached or glued or otherwise fixedly connected to a proximal end of the plunger rod 30A.

Turning to FIGS. 7A-E, the handle 10 includes a plunger rod stabilizing member 142 having a round hollow passage 149 formed therein. The rod stabilizing member 142 has two flange-like members 65A and 65B. The lower portions of the flange-like members 65A and 65B are shaped to fit into corresponding slots 144A and 144B formed in the proximal end of the second housing half 35B. The upper portions of the flange-like members 65A and 65B are shaped to fit within similar slots (not shown) formed in the proximal end of the first housing half 35A. When the handle 10 is assembled, the rod stabilizing member 142 is affixed within the housing 35 such that the rod stabilizing member is immovably disposed within the proximal end of the housing 35 such that the lower parts of the flange-like members 65A and 65B are disposed within the slots 144A and 144B of the lower housing half 35B and the upper parts of the flange-like members 65A and 65B are disposed within the slots (not shown) formed in the lower housing half 35B. The prong 40A of the locking mechanism 40 is movably disposed within a first recess 60A of the rod stabilizing member 142 and the prong 40B is of the locking mechanism 40 is movably disposed within a second recess 60B of the rod stabilizing member 142 (see FIGS. 7A-7E for details). The recesses 60A and 60B hold the prongs 40A and 40B, allowing them to slide freely in the longitudinal directions (proximal and distal) while stabilizing the prongs by restricting excessive lateral movements of the prongs 40A and 40B during movement within the housing 35.

When the catheter system 1 is in the assembled state, the hollow plunger rod 30A is slidably and movably disposed within the round hollow passage 149 of the rod stabilizing member 142 such as to support the proximal end of the hollow plunger rod 30A and to stabilize the movements of the hollow plunger rod 30A within the handle 10. The proximal end of the hollow plunger rod 30A has a recess 30C formed therein which fits into a narrow slot 55A formed within the slotted plate 55 disposed at the end of the pulling knob lower half 36B. When the pulling knob 36 is fully assembled into the assembled handle 10, the recess 30C of the hollow plunger rod 30A is disposed within the narrow slot 55A of the slotted plate 55 such that when the pulling knob 36 is assembled, and pulled proximally, the plunger rod 30A moves proximally as it is pulled by the slotted plate 55.

The proximal end of the inner conduit 17 is sealingly attached within the distal portion of the hollow tubular space formed within the hollow plunger rod 30A and extends distally from the distal opening thereof. The attaching of the inner conduit 17 within the distal portion of the hollow plunger rod 30A may be performed, for example, with a suitable adhesive or by any other method of attachment known in the art. The inner conduit 17 is adapted to move longitudinally (along the axis x) together with the hollow plunger rod 30A to which it is attached in a proximal direction within the cylindrical draw tube 20 and may be sealingly attached at its proximal end to the insertion port 33 which provides access to the lumen of the inner conduit 17. Alternatively, the proximal end of the inner conduit may be attached or glued within the hollow lumen of the hollow plunger rod 30A such that the inner conduit 17 only partially extends into the distal portion of the lumen of the hollow plunger rod 30A and does not fully extend therethrough.

The insertion port 33 may or may not be fixedly attached to the pulling knob 36 (for example by a suitable adhesive, or the like). Thus, when the plunger rod 30A is proximally pulled for intussuscepting of balloon 5, the inner conduit 17 is also pulled proximally therewith. Optionally, the inner conduit 17 may extend through the entire length of the hollow plunger rod 30A and may be sealingly attached to the inside surface of the hollow space within the hollow plunger rod 30A by the use of adhesives or other means of sealing attachment. In this case, the inner conduit 17 extends distally from the hollow plunger rod 30A and is movably disposed within the lumen of the outer conduit 18. The inner conduit 17 also extends proximally from the proximal end of the hollow plunger rod 30A and passes within the lumen of the draw tube 20. In this alternative embodiment, the insertion connector 33 is connected to the proximal end of the inner conduit 17.

When the plunger assembly 30 (including the hollow plunger rod 30A) is proximally moved, the inner conduit 17 is proximally retracted relative to the outer conduit 18 and intussuscepting of the balloon 5 occurs. Longitudinal proximal movement of the plunger assembly 30 is achieved by proximal pulling of the pulling knob 36 to which the plunger assembly 30 is attached.

Turning to FIGS. 8A and 8B which are a schematic isometric view and a top view, respectively, illustrating some of the components of the balloon catheter system of FIG. 1, after full proximal retraction of the plunger rod, in accordance with an embodiment of the of the catheter systems of the present application. In FIGS. 8A-8B the first housing half 35A and the first half 36A of the pulling knob 36 have been removed to allow better understanding of the proximal movement of some of the parts disposed within the handle 10. The balloon 5 and the inner conduit 17 and outer conduit 18 are not shown for the sake of clarity of illustration. In the top view of FIG. 8B, the prong 40A may be seen pulled maximally in the proximal direction such that the stopping members 43C and 43D are engaged with the stopping members 57A and 57B, respectively (note that in this state, in the fully assembled handle 10, the stopping members 44C and 44D of the prong 40B (which are not seen in the top view of FIG. 8B) are engaged with the corresponding stopping members of the first half 35A of the housing 35.

During proximal retraction of inner tube 17, the distal portion of the balloon 5 collapses and outer surface portions of the balloon 5 are folded inwardly over the distal end of the inner tube 17 and thereafter over itself as further portions of the balloon 5 collapse. The proximal retraction of the inner tube 17 and the resulting inward folding of the balloon 5 shorten the overall length of the inflated balloon which reduces the volume of the inflated balloon. Consequently, the pressure of the inflating fluids increases, which may result in a considerable pressure increase within the balloon 5 and in the lumen 18B between the inner tube 17 and the outer tube 18. However, inflation fluid flows from the balloon through the lumen 25 towards the fluidic system 11. When reaching fluidic system 11, the inflation fluid passes through the lumen 25 and into the cavity 22 in the three-way connector 11B and then into the cylindrical draw tube 20.

Preferably, but not obligatorily, the inner diameter of the draw tube 20 is equal to or close to the inner diameter of the inflated balloon 5 (as it is at the nominal inflation pressure of the balloon 5). Thus, after inflation of the balloon 5 through the fluid port 11A and sealing of the fluid port 11A by a closing a stopcock attached thereto (not shown) or by leaving the indeflator (not shown) connected to the fluid port 11A, when the plunger assembly 30 moves proximally, the gasket 29 slides proximally increasing the volume of the expandable cavity 31 within the draw tube 20 by a volume which is substantially equal to the excess fluid ejected from the balloon 5 by the same proximal movement of the inner conduit 17 which caused the intussuscepting of the balloon 5 which in turn ejected a volume of inflation fluid from the in-folding balloon 5. Thus, during the intussuscepting of the balloon 5, the volume of inflation fluid ejected from the balloon 5 due to a pulling of the plunger assembly 30 proximally by any distance, is substantially equal to the increase in volume of the space of the expandable cavity 31 due to the proximal movement of the plunger assembly 30 within the draw tube 20 by exactly the same distance. As substantially all the volume ejected from the balloon 5 at any distance of proximal pulling the plunger assembly 30 is accommodated within the new volume added to the expandable cavity 31, there is substantially no pressure increase within the lumen of the balloon 5 and the lumen formed between the inner conduit 17 and the outer conduit 18. After intussuscepting of the balloon 5 has been completed, the balloon 5 may be deflated by removing the inflation fluid through fluid port 11A, as disclosed hereinabove.

In accordance with an embodiment of the handle of the present application, the cylindrical draw tube 20 has an inner diameter D2 such that when the plunger assembly 30 is pulled proximally and travels the predetermined drawing distance L, the volume of inflation fluid flowing (drawn) into the cylindrical draw tube is substantially equal to the volume of fluid displaced from balloon 5 due to intussuscepting of the balloon. The drawing distance L may be made equal to, or shorter than, a length L1 of the balloon 5, and optionally the cross-sectional area of the lumen of the cylindrical draw tube 20 may be selected according to a diameter D1 of the (inflated) balloon 5. For example, the drawing distance L may be equal to or slightly smaller than the length L1 of balloon 5 (which allows for proper invagination of the balloon when the plunger rod assembly is pulled the drawing distance L) and the inner diameter D2 of the cylindrical draw tube 20 is selected accordingly to allow for the volume of inflation fluid displaced from balloon 5 to be accommodated within the extra space formed within the cylindrical draw tube 20 by the proximal movement of the plunger assembly 30. Optionally, the outer diameter of the cylindrical draw tube 20 may also be varied. As the volume of fluid drawn into the cylindrical draw tube 20 is substantially equal to the volume displaced from the balloon 5, there is no substantial change in the pressure in the cavity 20 and in the balloon 5, enabling the balloon catheter system 1 to be safely operated without a need for an overpressure valve and/or other adaptations for overpressure relief. This handle design advantageously simplifies catheter manufacturing and assembly.

In accordance with an embodiment of the handle of the present application, the double pronged locking mechanism 40 is additionally adapted to controllably move the plunger assembly 30 the predetermined drawing distance L when the pulling knob 36 is pulled in the proximal direction (aside from the safety features included in the double prong and previously described). When the pulling knob 36 is pulled in a proximal direction, away from the housing 35, as previously described, the double pronged locking mechanism 40 and the plunger rod assembly 30 (which are attached to the pulling knob 36) are also pulled longitudinally in the proximal direction. Therefore, by including features in the locking mechanism 40 which limit the proximal movement thereof inside the housing 35 to the drawing distance L, the proximal movement of the pulling knob 36 and of the plunger rod 30 is also restricted to the drawing distance L. Furthermore, the proximal movement of the inner conduit 17 relative to the outer conduit 18 is also restricted to the drawing distance L. The term "restricted" denotes that the maximal movement of the plunger assembly 30 and of the inner conduit 17 within the outer conduit 18 cannot exceed the drawing distance L.

Turning to FIGS. 5A-5C, the prong 40A includes two stopping members 43C and 43D formed therein which protrude sideways flanking distal locking member 41C. Prong 40B comprises two stopping members 44C and 44D formed therein which protrude sideways flanking distal locking member 42B (it is noted that the stopping member 44D is not seen in the top view of FIG. 5C nor in the isometric view of FIG. 5A. However it is similar in structure and dimensions to the corresponding stopping member 43C of the prong 40A). When the pulling knob 36 is pulled proximally over the drawing distance L, the stopping members 44C and 44D in prong 40B engage with stopping members 57A and 57B formed at a proximal end of second housing half 35B preventing the prong 40B from being pulled further. Similarly, the stopping members 43C and 43D in prong 40A engage with similar stopping members (not shown) formed at a proximal end of first housing half 35A. Thus, the position of the stopping members 43C, 43D and 44C, 44D, along the prong 40A and 40B, respectively, determines the maximal proximal pulling distance (drawing distance) L of the plunger assembly 30 within the cylindrical draw tube 20, and determines a maximal proximal movement of the inner conduit 17 relative to outer conduit 18. It is noted that the exact position of the locking members 41C relative to the position of the stopping members 43C and 43D on the prong 40A is arranged such that when the stopping members 43C and 43D are engaged with the stopping members 57A and 57B of the second housing half 35B, the locking member 41C is seated or engaged (locked) within the locking slot 46A of the first housing half 35A.

Thus, the position of the locking member 41C relative to the stopping members 43C and 43D may be slightly different than the position shown in FIGS. 5A-5C, depending on the actual distance between of the stopping members 57A and 57B and the slot 46B of the second housing half 35B. For similar reasons, the position of the locking member 41D relative to the stopping members 44C and 44D may depend on the actual distance between of the stopping members 57A and 57B and the slot 46B.

It is noted that while the locking mechanism 40 includes several safety features and is adapted to perform several locking functions for preventing unintentional or accidental movements of the plunger assembly 30, this is achieved while the entire locking mechanism 40 is disposed outside the fluidic system 11 and as such the locking mechanism 40 does not come into contact with the inflating fluid held inside the fluidic system 11 at any time. The locking mechanism 40 does not penetrate into the internal space of the fluidic system 11 neither does it penetrate the walls of the outer conduit 18. Furthermore, the locking mechanism 40 does not come into contact with the inner conduit 17 at any time. This is advantageous since it reduces or eliminates the possibility of leaking of the inflating fluid from the fluidic system 11 and substantially reduces the possibility of unintentional or premature depressurizing of the balloon 5 due to such leaks of inflating fluid.

Catheter systems such as, for example, the balloon catheter system 1, may be used with balloons of different sizes by using in handle 10 a double pronged locking mechanism 40 comprising suitably positioned stopping members (such as, for example, the stopping members 43C, 43D, 44C and 44D, or any combination thereof) adapted to terminate pulling at different drawing distances L. Optionally, the cylindrical draw tube 20 of the handle 10 may be selected to have a suitable inner diameter and a respective suitable gasket 29 (having a suitable outer diameter of the gasket to sealingly fit in the inner diameter D2 of the cylindrical draw tube 20) such that the space formed within the draw tube 20 by pulling the plunger 30 proximally will accommodate the amount of inflation fluid ejected from the balloon having the selected diameter without causing any substantial pressure increase within the catheter lumen and within the balloon. Therefore, the balloon catheter system 1 may be used with a large variety of balloons of different sizes by using an assortment of locking mechanism 40 with differently positioned stopping members and locking members, and, optionally, using different types of cylindrical draw tubes 20 with different inner diameters D2 (and further optionally with different outer diameters of the draw tubes 20), and a suitable gasket 29 to seal the draw tube 20. All other components of the handle 10 remain essentially the same.

This feature is advantageous because, by keeping many parts of the handle 10 essentially the same, and changing only the double pronged locking mechanism 40 (with suitable distance L separating the locking member 41A from the locking member 41C along the prong 40A and the locking member 41B from the locking member 41D along the prong 40B, in order to match the drawing distance L in accordance with the actual length of the balloon 5 and changing the position of the stopping members 43C and 43D along the prong 40A and of the stopping members 44C and 44D along the prong 40B in order to match the drawing distance L in accordance with the actual length of the balloon 5), the position of the locking slot 46A along the first housing half 36A (to match the new position of the locking member 41A along the prong 40A), the position of the locking slot 46B along the second housing half 36B (to match the new position of the locking member 41B along the prong 40B), the inner diameter of the cylindrical draw tube 20, and the outer diameter of the gasket 29 (to match the inner diameter of the draw tube 20), it is possible to minimize the number of different parts required for manufacturing series of different catheter systems having different balloon sizes (such as, for example different balloon diameters and/or different balloon lengths).

It is noted that in accordance with one preferred embodiment of the catheter system of the present application, the position of locking slot 46A on the first housing half 35A is fixed. Similarly, the position of locking slot 46B on the second housing half 35B is fixed. In this embodiment, the positions of both locking slots 46A and 46B do not change in catheter systems having different balloon lengths and different locking mechanisms and what is changed in catheter systems having different length of balloons is the positions of the distal locking members 41C, 41D and of the stopping members 43C, 43D, 44C and 44D on the prongs 40A and 40B, respectively, as disclosed hereinabove.

For example, by using a series of different cylindrical draw tubes 20 all having an identical outer diameters (standardized to fit within the lumen diameter of the distal end 11D of the fluidic system 11) but different inner diameters D2 and a matching set of different gaskets 29 having different outer diameters (to match the differing inner diameters of the different draw tubes 20), together with a set of different double pronged locking mechanisms 40 having various different positions of the stopping members (43C, 43D and 44C, 44D) and locking members (41A and 41B, respectively) along the prongs (40A and 40B, respectively), the cost of manufacturing of such a plurality of systems with different balloon sizes is substantially reduced and made more efficient since the required stock of different parts is greatly reduced.

Furthermore, by using sufficiently large dimensions of the housing 35, the locking mechanism 40, the plunger assembly 30 and the draw tube 20, it is possible to use a single standard size of the handle 10 to accommodate the largest practical balloon length and diameters, such that the same parts may be used for a large practical variety of balloon lengths and balloon diameters while the only parts that need to be changed to match different balloon diameters are the locking mechanism 40 (by suitably changing the position of the stopping members 43C, 43D along the prong 40A and the position of the stopping members 44C, 44D along the prong 40B to change the drawing distance L to match the balloon length if necessary), the draw tube member 20 (by changing the inner diameter and, optionally, the outer diameter, thereof to match the balloons inflated diameter, if necessary) and the outer diameter of the gasket 29 to match the inner diameter of the draw tube 20, if necessary).

In a non-limiting example, if the longest practically usable balloon length is 300 mm and the largest usable balloon diameter (crossing diameter) is 15 mm, the dimensions of the housing 35, the locking mechanism 40, the plunger assembly 30 and the draw tube 20 are made long enough and large or wide enough to enable a drawing distance L of 300 mm (or lower) and the outer diameter of the draw tube 20 is made large enough to ensure that the inner diameter of the draw tube 20 may be large enough to ensure that the amount of the fluid ejected from the balloon 5 during full intussuscepting thereof will be accommodated by the additional space added to the cavity 22 by proximal movement of the plunger assembly 30 by the drawing distance L.

By using such suitable choice of handle component dimensions it is possible to use the handle 10 for making a full range of the catheter systems 1 as described hereinabove which may include the full desired range of balloon 5 lengths (300 mm or less, in the particular non-limiting example given hereinabove) and the full desired range of balloon inflated diameters (of 15 mm or smaller diameters, in the particular non-limiting example given hereinabove), in any desired combination of balloon length and balloon diameter. In catheter systems having balloon lengths smaller than 300 mm, the only part that needs to be changed (assuming a constant balloon diameter), is the locking mechanism 40 (by suitably selecting a locking mechanism 40 having properly positioned stopping members 43C, 43D and 44C, 44D).

In catheter systems 1 having balloon diameters smaller than 15 mm, the only parts that need to be changed (assuming a constant balloon length), is the draw tube 20 and the gasket 29 (by suitably selecting a draw tube 20 having properly sized inner diameter and by matching a suitably sized gasket 29 to fit the selected inner diameter of the draw tube 20).

Any desired combination of balloon length and balloon diameter within the above indicated (exemplary and non-limiting) ranges of balloon lengths and balloon diameters may thus be used in the catheter systems 1 by appropriate selection of one or more of the locking mechanism 40, and/or draw tube 20 and gasket 29 combinations having appropriate dimensions and configuration as disclosed hereinabove.

Figure 9:
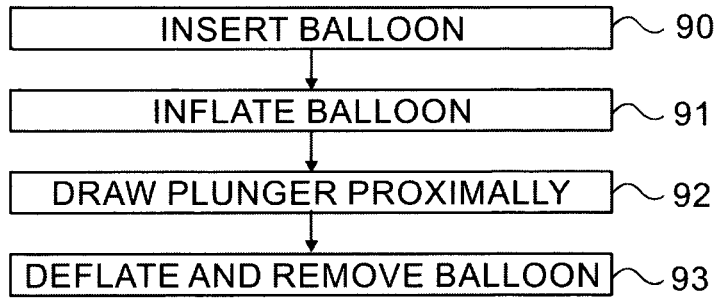
FIG. 9 is a schematic flow diagram illustrating steps of a method of operating the balloon catheter system of FIG. 1, in accordance with an embodiment of a method of using the catheter systems of the present application.

Reference is made to FIG. 9 which illustrates a flow diagram of a method of operating balloon catheter system 1, in accordance with an embodiment of the present disclosure. The method described is not intended to be limiting in any way, form or manner, and a person skilled in the art may readily appreciate that the steps described, including their sequence, may be varied.

[STEP 90] The physician (or the operator) inserts the balloon 5 and the outer conduit 18 into a blood vessel of a patient (preferably, but not obligatorily, over a guide wire 33A) and guides the balloon 5 to the treatment site (not shown) as is known in the art. At this stage, the pulling knob 36 is the retracted and locked state as illustrated in FIG. 1, and the protruding locking members 41A and 41B are engaged in the locking slot 46A in first housing half 35A and in the locking slot 46B in second housing half 35B.

[STEP 91] The physician inflates balloon 5 by using an indeflator (not shown) attached to the fluid port 11A to inject inflation fluid via the fluid port 11A into the lumen 25 between the outer conduit 18 and the inner conduit 17 and into the balloon 5. The plunger gasket 29 in the plunger assembly 30 prevents the inflation fluid from flowing from cavity 22 in the three-way connector 11B through the second end 11D into the cylindrical draw tube 20. Once the balloon 5 is fully inflated and anchored inside the blood vessel, inflation port 11A is sealed (either by leaving the indeflator attached to the fluid port 11A or by closing a suitable stopcock or three way valve connected between the fluid port 11A and the indeflator), and the physician may perform the required medical procedures inside the blood vessel. Additionally or alternatively, the inflating of the balloon 5 may be part of the treatment if the balloon 5 is used to open or distend an occlusion in the blood vessel. Alternatively or additionally the balloon 5 may also carry a stent which is deployed in the target site by the inflating of the balloon 5 to expand the stent as is known in the art.

[STEP 92] Once the medical procedures inside the blood vessel are completed, the physician simultaneously presses the releasing members 48A and 48B causing the protruding locking members 41A and 41B to be released from engagement in the locking slots 46A and 46B, respectively, allowing the pulling knob 36 to be pulled proximally and the double pronged locking mechanism 40 to slide proximally within the housing 35 as disclosed in detail hereinabove. The physician pulls the pulling knob 36 proximally until the pulling knob 36 stops and cannot be pulled any further. When the pulling knob 36 stops, the stopping members 44C and 44D of the prong 40B engage with the stopping members 57A and 57B, respectively, which are formed at a proximal end of the lower housing half 35B, while the stopping members 43C and 43D of the prong 40A engage with similar stopping members (not shown) formed at a proximal end of the first housing half 35A. Additionally, the distal locking members 42A and 42B engage within the locking slots 46A and 46B, respectively, and the double pronged locking mechanism 40 and the pulling knob 36 are immovably locked in place (in a protracted state) relative to the housing 35, preventing the pulling knob 36 and the double pronged locking mechanism 40 from being accidentally or unintentionally pushed back (distally) into the housing 35.

By pulling the knob 36 proximally until it stops, the plunger assembly 30 has been proximally drawn within cylindrical draw tube 20 by the drawing distance L, proximally pulling the inner conduit 17 relative to the outer conduit 18 causing the invaginating and intussuscepting of the balloon 5 (as shown in detail in US published patent application No. 2007/0083158). The volume of inflation fluid forced out of the balloon 5 by the intussuscepting, occupies a similar volume inside the cylindrical draw tube 20 and the pressure inside balloon catheter 1 and the balloon 5 remains substantially unchanged.

[STEP 93] The physician may now proceed to remove balloon 5 from the blood vessel of the patient. Prior to removal, the intussuscepted balloon 5 is deflated through the inflation port 11A by opening the inflation port 11A (or a three-way stopcock connected to the fluid port 11A) or by using the indeflator or other syringe-like device connected to the inflation port 11A. After the inflation fluid is removed and the balloon 5 is in a substantially deflated state, the physician may remove the deflated balloon 5 including the inner conduit 17 and the outer conduit 18, and possibly the guide wire 33A (if the guide wire 33A was left within the catheter during treatment), from the blood vessel, withdrawing the balloon catheter system 1 from the patient's body.

Figure 10:
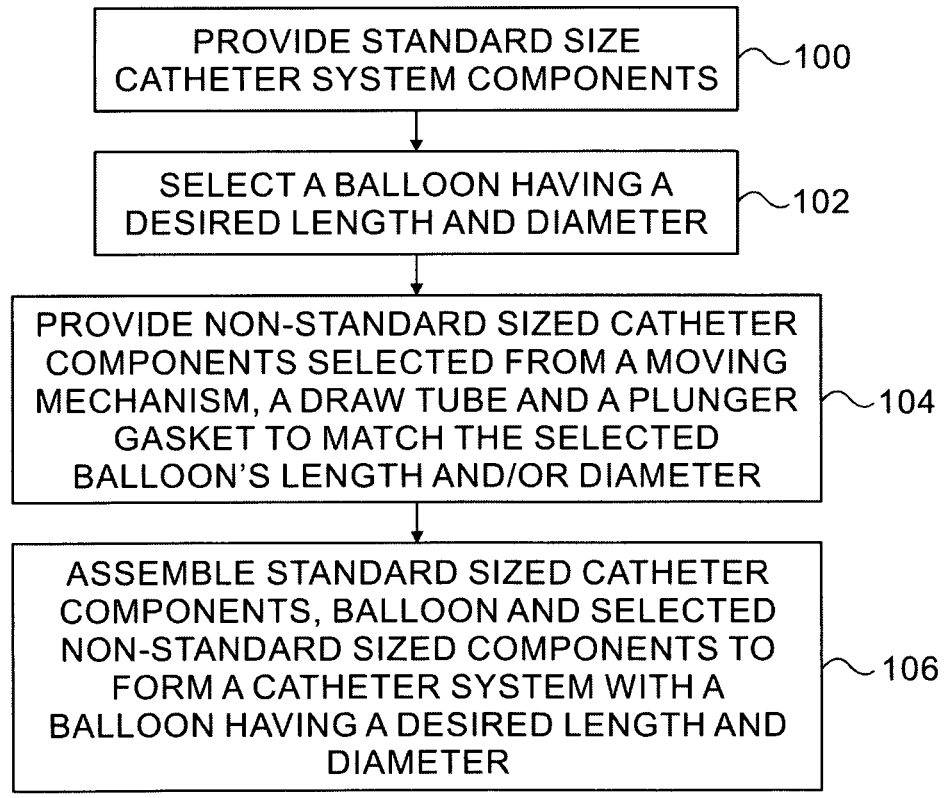
FIG. 10 is a schematic flow diagram illustrating steps of a method of constructing the balloon catheter system of FIG. 1, in accordance with an embodiment of the methods of the present application.

Reference is now made to FIG. 10 which is a schematic flow diagram illustrating steps of a method of constructing the balloon catheter system of FIG. 1, in accordance with an embodiment of a method of the present application.

In accordance with an embodiment of the method of FIG. 10, the assembling of an intussusceptible balloon catheter having a desired balloon length and balloon diameter is performed by providing a plurality of standard catheter system components (Step 100). The standard components are components which do not vary in sized or shape and which are similar in all the catheter systems irrespective of the size and/or length of the balloon used in the catheter system.

The standard components may include all the parts of the handle except the locking mechanism 40, the draw tube 20, and the plunger gasket 29. The assembling person or machine (if the assembling is automatic performed by machine) selects an inflatable balloon 5 having a desired length and diameter, (step 102).

After selection of the balloon, the person (or assembling machine) provides a plurality of non-standard components of the catheter system and selects from the plurality of available non-standard components a locking mechanism 40, a draw tube 20 a plunger gasket 29 an first housing half 35A and a second housing half 35B, to match the length and the diameter of the balloon 5 (or inflatable element) selected in the step of selecting (step 104). The selection of the non-standard parts is performed such that the positions of the locking member 41C on the prong 40A and the position of the locking member 44C on the prong 40B are matched to the position of the corresponding locking slot 46A on the first housing half 35A and the position of the locking slot 46B on the second housing half 35B, respectively and that the position of the stopping members 43C and 43D on the prong 40A and the positions of the stopping members 44C and 44D on the prong 40B are matched to the desired Drawing distance L. Thus, the non-standard components of the system are such parts or components that may be different in size or shape or configuration in different catheter systems having balloons of different balloon length and/or different balloon diameter. For example, different locking mechanisms may differ from each other by the different spacing of the locking members (such as, for example, the locking member 41A and 41C on the prong 40A) and by the different positioning of the stopping members along the prong(s) of the locking mechanism (such as, for example, by having different positions of the stopping members 43C and 43D on the prong 40A). In another example, the gaskets 29 may vary from each other by having different outer gasket diameters in catheters having different balloon diameters. In another example, the different hollow drawing members 20 may vary from each other by having different diameters D2 of their lumens to match the different diameters of the gaskets 29.

The assembling person (or assembling machine) then assembles the standard sized components, the balloon the locking mechanism, the draw tube the plunger gasket and the first and second housing halves 35A and 35B, respectively to form the catheter system 1 (step 106).

Typically, but not obligatorily, the standard sized components of the handle may include the collar 37, the nose piece 38, The first and second housing halves 35A and 35B, the pulling knob 36 (including both the first and the second pulling knob halves 36A and 36B), the three way connector 11B of the fluidic system 11, the plunger rod 30A and the rod stabilizing member 142.

It is noted that while the locking mechanism 40 disclosed above is structured to have multiple safety mechanisms to increase the safety of operating the catheter system 1, this is not obligatory and other structures of the handle may be implemented which may be still safely operated while simplifying the design of certain parts.

In accordance with one possible embodiment of the catheter system the locking mechanism may have a reduced number of stopping members and/or a reduced number of locking members. For example, the prong 40B may be implemented as a smooth prong by eliminating the stopping members 44C and 44D and the locking members 41B and 41D. In such an embodiment, the locking action will be performed only by the remaining locking members 41A and 41C of the remaining prong 40A and the stopping action will be performed by the stopping members 43C and 43D of the remaining prong 40A. In such an embodiment locking slot 46B of the second housing half 35B may be eliminated as well as it becomes redundant.

Similarly, the prong 40A may be implemented as a smooth prong by eliminating the stopping members 43C and 43D and the locking members 41C and 41A. In such an embodiment, the locking action will be performed only by the remaining locking members 41B and 41D of the remaining prong 40B and the stopping action will be performed by the stopping members 44C and 44D of the remaining prong 40B. In such an embodiment locking slot 46A of the first housing half 35A may be eliminated as well as it becomes redundant.

In accordance with other embodiments, only the stopping members may be eliminated from only one of the prongs 40A or 40B, while all four locking members 41A, 41B, 41C and 41D are retained.

In accordance with other embodiments, only the locking members may be eliminated from only one of the prongs 40A or 40B, while all four stopping members 43A, 43B, 43C and 43D are retained.

It is noted that if one or both of the locking members are eliminated from a single prong (either 40A or 40B) of the locking mechanism 40, the corresponding locking slot on the respective side of the half housing of the housing 35 may also be eliminated as it becomes redundant.

Thus, the moving member may be modified as desired or as deemed necessary by removing either locking members or stopping members or both locking members and stopping members, as long as at lease one stopping member is left on at least one prong of the locking mechanism. Using the configuration of the locking mechanism 40 with a plurality of locking members and a plurality of stopping members (as illustrated in FIGS. 5A-5C) is advantageous as it substantially improves the safety of operation of the catheter system, this configuration is not obligatory and embodiments of the catheter system 1 including locking mechanisms having a reduced number of locking members (or no locking members at all) may be constructed and used and are included within the scope of the catheter systems and handles of the present application.

Furthermore, while the preferred embodiment of the catheter systems disclosed herein above includes a double pronged locking mechanism 40, other embodiment of the catheters may be implemented by using single pronged locking mechanism. For Example, such a single pronged locking mechanism may be implemented by eliminating the flat linear part of the prong 40B such that the resulting modified locking mechanism includes only the elongated member of prong 40A, the releasing member 48A and the releasing member 48B. In such an embodiment of the moving member, the catheter system is operated similarly to the manner of operation of the system including the double pronged moving member 40 except that only the releasing member 48A needs to be pressed down by the operator in order to release the locking member 41A from the locking slot 46A in order to release the locking of the locking mechanism and pulling knob 36 and enable their proximal pulling by the operator. It is noted that in such a single pronged embodiment, The stopping of the proximal movement of the locking mechanism is achieved by engagement of the stopping members 41C and 41D with the stopping members included in the first housing half 35A (since in this embodiment the moving member does not include the prong 40B).

It is noted that the catheter system disclosed hereinabove is useful in all systems using an intussuscepting balloon known in the art, including, but not limited to the OVT catheter systems as disclosed in US published patent application No. 2007/0083158 and the rapid exchange catheter systems disclosed in US published patent application No. 2009/0204069. It will be apparent to the person skilled in the art that the construction and operation of the handle disclosed herein may be adapted for use in any intussuscepting balloon catheters having an inner conduit axially movable within an outer conduit.

The above examples and descriptions have of course been provided only for the purpose of illustration and are not intended to limit the invention in any way. As will be appreciated by the skilled person, the invention can be carried out in a great variety of ways, employing more than one technique from those described above, all without exceeding the scope of the present disclosure.

The invention claimed is:

1. A balloon catheter system having an intussuscepting balloon said catheter system comprising:
    an outer conduit;
    an inner conduit, suitable for passage over a guide wire, said inner conduit is disposed within the lumen of said outer conduit such that the longitudinal axes of said inner and outer conduits are substantially parallel, said inner conduit is positioned such that a distal tip of said inner conduit extends beyond a distal tip of said outer conduit, wherein said inner conduit is adapted for being moved along its longitudinal axis in relation to said outer conduit;
    an inflatable balloon having a balloon diameter and a balloon length, the proximal end of said balloon is sealingly attached to the outer surface of the distal tip of said outer conduit and the distal end of said balloon is sealingly attached to the outer surface of the portion of said inner conduit that extends beyond the distal tip of said outer conduit, wherein the distal end portion of said balloon is adapted for intussuscepting upon proximal movement of said inner conduit in relation to said outer conduit, said balloon is selected from a plurality of different balloons each having a unique combination of balloon length and balloon diameter; and
    a handle adapted for moving said inner conduit proximally within said outer conduit and for removing a volume of an inflation fluid from said balloon into an expandable chamber in said handle when said balloon is being intussuscepted in an inflated state such that during the intussuscepting of said balloon the pressure within said balloon and said expandable chamber remains substantially unchanged, said handle includes,
    a housing having standard dimensions,
    a hollow fluidic system disposed within said housing, said fluidic system includes a first end sealingly attached to said outer conduit and a second end sealingly attached to a hollow drawing member, said fluidic system also includes a fluidically sealable fluid port for introducing inflating fluid into said balloon through a space formed between said inner conduit and said outer conduit and for withdrawing said inflating fluid from said balloon through said fluidic system,
    a hollow plunger assembly movably disposed in said housing, said plunger assembly includes a hollow plunger rod surrounding said inner conduit and attached thereto, said hollow plunger rod is sealingly and movably disposed within said hollow drawing member to form said expandable chamber, said hollow drawing member is selected from a plurality of non-standard hollow drawing members having different inner diameters such that the inner diameter of said hollow drawing member is matched to the diameter of said balloon, said hollow plunger assembly also includes a gasket attached to said hollow plunger rod and sealingly disposed within said hollow drawing member and having a gasket diameter, said gasket is selected from a plurality of different gaskets such that the diameter of said gasket matches the inner diameter of said hollow drawing member, said inner conduit is attached to said plunger assembly, said plunger assembly is adapted to be partially pulled out of said housing to longitudinally proximally move said inner conduit within said outer conduit for intussuscepting said balloon and to expand said expandable chamber for accommodating inflating fluid ejected from said balloon during the intussuscepting thereof, and
    a locking mechanism movably disposed within said housing for controllably enabling and disabling the moving of said inner conduit within said outer conduit and the moving of said plunger assembly within said hollow drawing member, said locking mechanism is selected from a plurality of differently sized non-standard locking mechanisms to match said length of said balloon.

2. The balloon catheter system according to claim 1 wherein said locking mechanism comprises at least one elongated member having at least one stopping member, said at least one stopping member is positioned on said at least one elongated member to engage with at least one stopping member disposed at the proximal end of said housing such that the proximal moving of said plunger assembly is stopped at a maximal longitudinal proximal moving distance.

3. The balloon catheter system according to claim 1 wherein said locking mechanism comprises at least a first locking member disposed at the proximal end of said at least one elongated member, said at least first locking member is adapted to prevent the locking mechanism from being proximally pulled out of said housing by being locked within a locking slot formed in said housing.

4. The balloon catheter system according to claim 3 wherein said locking mechanism also comprises at least a second locking member disposed at the distal end of said at least one elongated member and spaced apart from said first locking member, said at least second locking member is adapted to prevent said locking mechanism from being distally pushed inside said housing when said second locking member is locked within said locking slot.

5. The balloon catheter system according to claim 1 wherein the locking mechanism comprises at least one releasing member operable to allow said locking mechanism and said plunger assembly to be proximally pulled away from said housing.

6. The balloon catheter system according to claim 1 wherein said locking mechanism is selected from a single pronged locking mechanism comprising one elongated member and a double pronged locking mechanism comprising two elongated members.

7. The balloon catheter system according to claim 6 wherein said locking mechanism is a double pronged locking mechanism comprising two elongated members flanking at least a portion of said plunger assembly.

8. The balloon catheter system according to claim 1 wherein said plunger assembly comprises a hollow plunger rod and a gasket attached to said plunger rod, said gasket is adapted to slidably and sealingly move inside said hollow drawing member to change the volume of said expandable chamber.

9. The balloon catheter system according to claim 1 wherein the hollow fluidic system comprises a hollow three-way connector.

10. The balloon catheter system according to claim 9 wherein the hollow three-way connector is shaped as a T-connector.

11. The balloon catheter system according to claim 9 wherein said hollow drawing member is a cylindrical tube sealingly attached within the proximal end of said three way connector.

12. The balloon catheter system according to claim 1 wherein said balloon catheter system further includes a pulling knob attached to said locking mechanism and to the proximal end of said plunger assembly for assisting the pulling and pushing of said locking mechanism and said plunger assembly.

13. The balloon catheter system according to claim 1 wherein said catheter system also comprises a locking mechanism stabilizing member immovably disposed within said housing for stabilizing the movement of said locking mechanism within said housing.

14. The balloon catheter system according to claim 13 wherein said locking mechanism stabilizing member has a hollow passage formed therein for stabilizing the movement of a hollow plunger rod included in said plunger assembly, said plunger rod is movably disposed within said hollow passage of said stabilizing member.

15. The balloon catheter system according to claim 1 wherein said housing comprises a first housing half and a second housing half.

16. The balloon catheter system according to claim 15 wherein said housing also comprises a nose piece for connecting the distal ends of said first housing half and said second housing half together and a collar for connecting the proximal ends of said first housing half and said second housing half together.

17. The balloon catheter system according to claim 1 wherein said handle comprises a pulling knob attached to said plunger assembly.

18. The balloon catheter system according to claim 17 wherein said pulling knob comprises a first pulling knob half and a second pulling knob half.

19. The balloon catheter system according to claim 17 wherein distal parts of said locking mechanism and of said plunger assembly are attached to said pulling knob.

20. A method for assembling the intussuscepting balloon catheter system according to claim 1 having a desired length and diameter of said balloon, the method comprising the steps of:
providing a plurality of standard sized catheter system components, said plurality of standard sized components comprises at least said housing, said plunger rod, said three-way hollow connector and a pulling knob;
selecting said inflatable balloon having a desired length and diameter, said balloon is sealingly attached to said outer conduit at the proximal end of said balloon and to said inner conduit at the distal end of said balloon, said inner conduit is movably disposed within said outer conduit;
providing a plurality of non-standard components of said catheter system and selecting from said plurality of non-standard components said locking mechanism constructed to match the length of said selected balloon, said hollow drawing member having an inner diameter matching the diameter of said balloon, said gasket having an outer gasket diameter matching the inner diameter of said hollow drawing member, to match the length and the diameter of said balloon selected in said step of selecting; and
assembling said standard components, said selected balloon, said selected locking mechanism, said hollow drawing member and said selected gasket to form said catheter system.

21. The method according to claim 20, wherein said locking mechanism comprises at least one elongated member having one or more stopping members therealong configured to engage with one or more housing stopping members formed in said housing of said catheter system and wherein said step of providing a plurality of non standard components comprises selecting a locking mechanism having said stopping members disposed at a position along said at least one elongated member such that when said locking mechanism is proximally moved within said housing, said stopping members engage with said one or more housing stopping members after traveling a drawing distance L substantially equal to or smaller than the length of the balloon selected in said step of selecting.

22. The method according to claim 20, wherein said hollow drawing member comprises a cylindrical hollow tube having a lumen with a lumen diameter, wherein said gasket has a diameter adapted to sealingly and movably fit within the lumen of said cylindrical hollow tube, and wherein said step of providing a plurality of non standard components comprises selecting a cylindrical hollow tube having a lumen diameter and a gasket having an outer diameter matching to said lumen diameter from said plurality of said non-standard components such that when said locking mechanism is proximally moved within said housing, the amount of an inflation fluid ejected from said selected balloon at any stage of the moving of said locking mechanism is accommodated within said lumen of said hollow drawing member without a substantial change in the pressure within said balloon and said catheter system.

23. A handle for use in a balloon catheter system having an intussuscepting balloon said catheter system comprising an outer conduit, an inner conduit suitable for passage over a guide wire, said inner conduit is disposed within the lumen of said outer conduit such that the longitudinal axes of said inner and outer conduits are substantially parallel, said inner conduit is positioned such that a distal tip of said inner conduit extends beyond a distal tip of said outer conduit, said inner conduit is adapted for being moved along its longitudinal axis in relation to said outer conduit. an inflatable balloon having a balloon diameter and a balloon length, the proximal end of said balloon is sealingly attached to the outer surface of the distal tip of said outer conduit and the distal end of said balloon is sealingly attached to the outer surface of a portion of said inner conduit that extends beyond the distal tip of said outer conduit, wherein a portion of the distal end of said balloon is adapted for intussuscepting upon proximal movement of said inner conduit in relation to said outer conduit, the handle comprising:
a housing having standard dimensions;
a hollow fluidic system disposed within said housing, said fluidic system includes a first end sealingly attachable to said outer conduit and a second end sealingly attached to a hollow drawing member, said fluidic system also includes a fluidically sealable fluid port for introducing inflating fluid into said balloon through a space formed between said inner conduit and said outer conduit and for withdrawing said inflating fluid from said balloon through said fluidic system;

a hollow plunger assembly movably disposed in said housing, said plunger assembly includes a hollow plunger rod surrounding said inner conduit and attached thereto, said hollow plunger rod is sealingly and movably disposed within said hollow drawing member to form an expandable chamber, said hollow drawing member is selected from a plurality of non-standard hollow drawing members having different inner diameters such that the inner diameter of said hollow drawing member is matched to the diameter of said balloon, said hollow plunger assembly also includes a gasket attached to said hollow plunger rod and sealingly disposed within said hollow drawing member and having a gasket diameter, said gasket is selected from a plurality of non-standard different gaskets such that the diameter of said gasket matches the inner diameter of said hollow drawing member, said inner conduit is attached to said plunger assembly, said plunger assembly is adapted to be partially pulled out of said housing to longitudinally proximally move said inner conduit within said outer conduit for intussuscepting said balloon and to expand said expandable chamber for accommodating inflating fluid ejected from said balloon during the intussuscepting thereof; and a locking mechanism movably disposed within said housing for controllably enabling and disabling the moving of said inner conduit within said outer conduit and the moving of said plunger assembly within said hollow drawing member.

24. The handle according to claim 23 wherein said locking mechanism comprises at least one elongated member having at least one stopping member, said at least one stopping member is positioned on said at least one elongated member to engage with at least one stopping member disposed at the proximal end of said housing such that the proximal moving of said plunger assembly is stopped at a maximal longitudinal proximal moving distance.

25. The handle according to claim 23 wherein said locking mechanism comprises at least a first locking member disposed at the proximal end of said at least one elongated member, said at least first locking member is adapted to prevent the locking mechanism from being proximally pulled out of said housing by being locked within a locking slot formed in said housing.

26. The handle according to claim 25 wherein said locking mechanism also comprises at least a second locking member disposed at the distal end of said at least one elongated member and spaced apart from said first locking member, said second locking member is adapted to prevent said locking mechanism from being distally pushed inside said housing when said second locking member is locked within said locking slot.

27. The handle according to claim 23 wherein the locking mechanism comprises at least one releasing member operable to allow said locking mechanism and said plunger assembly to be proximally pulled away from said housing.

28. The handle according to claim 23 wherein said locking mechanism is selected from a single pronged locking mechanism comprising one elongated member and a double pronged locking mechanism comprising two elongated members.

29. The handle according to claim 28 wherein said locking mechanism is a double pronged locking mechanism comprising two elongated members flanking at least a portion of said plunger assembly.

30. The handle according to claim 23 wherein said plunger assembly comprises a hollow plunger rod and a gasket attached to said plunger rod, said gasket is adapted to slidably and sealingly move inside said hollow drawing member to change the volume of said expandable chamber.

31. The handle according to claim 23 wherein the hollow fluidic system comprises a hollow three-way connector.

32. The handle according to claim 31 wherein the hollow three-way connector is shaped as a T-connector.

33. The handle according to claim 31 wherein said hollow drawing member is a cylindrical tube sealingly attached within a proximal end of said three way connector.

34. The handle according to claim 23 wherein said handle further includes a pulling knob attached to said locking mechanism and to a proximal end of said plunger assembly for assisting the pulling and pushing of said locking mechanism and said plunger assembly.

35. The handle according to claim 23 wherein said catheter system also comprises a locking mechanism stabilizing member immovably disposed within said housing for stabilizing the movement of said locking mechanism within said housing.

36. The handle according to claim 35 wherein said locking mechanism stabilizing member has a hollow passage formed therein for stabilizing the movement of a hollow plunger rod included in said plunger assembly, said plunger rod is movably disposed within said hollow passage of said stabilizing member.

37. The handle according to claim 23 wherein said housing comprises a first housing half and a second housing half.

38. The handle according to claim 37 wherein said housing also comprises a nose piece for connecting the distal ends of said first housing half and said second housing half together and a collar for connecting the proximal ends of said first housing half and said second housing half together.

39. The handle according to claim 23 wherein said handle comprises a pulling knob attached to said plunger assembly.

40. The handle according to claim 39 wherein said pulling knob comprises a first pulling knob half and a second pulling knob half.

41. The handle according to claim 39 wherein distal parts of said locking mechanism and of said plunger assembly are attached to said pulling knob.

* * * * *